(12) United States Patent
Rahman et al.

(10) Patent No.: US 9,732,157 B2
(45) Date of Patent: Aug. 15, 2017

(54) METHODS FOR THE DEVELOPMENT OF METZINCIN-SELECTIVE CATALYTIC CLEFT DIRECTED ANTIBODIES FOR THERAPEUTIC AND DIAGNOSTIC APPLICATIONS

(76) Inventors: Salman Rahman, London (GB); Yatin Patel, London (GB)

( * ) Notice: Subject to any disclaimer, the term of this patent is extended or adjusted under 35 U.S.C. 154(b) by 16 days.

(21) Appl. No.: 13/876,966

(22) PCT Filed: Oct. 1, 2011

(86) PCT No.: PCT/IB2011/002860
§ 371 (c)(1),
(2), (4) Date: Jun. 17, 2013

(87) PCT Pub. No.: WO2012/042391
PCT Pub. Date: Apr. 5, 2012

(65) Prior Publication Data
US 2013/0273051 A1 Oct. 17, 2013

Related U.S. Application Data

(60) Provisional application No. 61/389,176, filed on Oct. 1, 2010.

(51) Int. Cl.
*C07K 16/40* (2006.01)
*C07K 16/28* (2006.01)
*G01N 33/573* (2006.01)

(52) U.S. Cl.
CPC .......... *C07K 16/40* (2013.01); *C07K 16/2896* (2013.01); *G01N 33/573* (2013.01); *C07K 2317/34* (2013.01)

(58) Field of Classification Search
CPC .... C07K 16/40; C07K 16/30; C07K 14/8146; C07K 2317/34; C07K 2316/96; A61K 2039/505
See application file for complete search history.

(56) References Cited

U.S. PATENT DOCUMENTS

| 6,344,352 B1 | 2/2002 | Merkulov et al. |
| 2004/0102392 A1 | 5/2004 | Bennett et al. |
| 2011/0117090 A1 | 5/2011 | Rahman et al. |

FOREIGN PATENT DOCUMENTS

| EP | 1 609 804 A1 | 12/2005 | |
| EP | 2 174 956 A1 | 4/2010 | |
| EP | 2 186 894 A1 | 5/2010 | |
| WO | WO 02/066057 A2 | 8/2002 | |
| WO | WO 2004/024089 A2 | 3/2004 | |
| WO | WO 2009/101968 A1 | 8/2009 | |
| WO | WO 2009/118660 | * 10/2009 | ............ C07K 16/00 |
| WO | WO 2009/118660 A2 | 10/2009 | |

OTHER PUBLICATIONS

Georgiadis et al. (Bioorganic and Medicinal Chemistry, 16: 8781-8794, 2008).*
Buckler et al. (Drug Discovery Today, 13: 318-324, 2008).*
Mariuzza et al. (Annu. Rev. Biophys. Biophys. Chem. 1987; 16: 139-159).*
Zheng et al. (Cancer Biology and Therapy, 8(11): 1045-1054, Jun. 2009).*
International Preliminary Report on Patentability for PCT/IB2009/005613 mailed Oct. 7, 2010.
International Preliminary Report on Patentability for PCT/IB2011/002860 mailed Apr. 11, 2013.
International Search Report and Written Opinion for PCT/IB2009/005613 mailed Dec. 29, 2009.
International Search Report and Written Opinion for PCT/IB2011/002860 mailed Jul. 3, 2012.
Aktas et al., Aspirin induces platelet receptor shedding via ADAM17 (TACE). J Biol Chem. Dec. 2, 2005;280(48):39716-22. Epub Sep. 22, 2005.
Alfandari et al., ADAM 13 is a metalloprotease required for cranial neural crest-cell migration. Curr Biol. Jun. 26, 2001;11(12):918-30.
Alfandari et al., ADAM 13: a novel ADAM expressed in somitic mesoderm and neural crest cells during Xenopus laevis development. Dev Biol. Feb. 15, 1997;182(2):314-30.
Bajou et al., The plasminogen activator inhibitor PAI-1 controls in vivo tumor vascularization by interaction with proteases, not vitronectin. Implications for antiangiogenic strategies. J Cell Biol. Feb. 19, 2001;152(4):777-84.
Bass et al., Regulation of urokinase receptor proteolytic function by the tetraspanin CD82. J Biol Chem. Apr. 15, 2005;280(15):14811-8. Epub Jan. 27, 2005.
Bellacosa et al., Activation of AKT kinases in cancer: implications for therapeutic targeting. Adv Cancer Res. 2005;94:29-86.
Blobel, ADAMs: key components in EGFR signalling and development. Nat Rev Mol Cell Biol. Jan. 2005;6(1):32-43.
Blobel, Metalloprotease-disintegrins: links to cell adhesion and cleavage of TNF alpha and Notch. Cell. Aug. 22, 1997;90(4):589-92.
Böhm et al., ADAM15 modulates outside-in signalling in chondrocyte-matrix interactions. J Cell Mol Med. Aug. 2009;13(8B):2634-44.
Busso et al., Extravascular Coagulation and the Plasminogen Activator/Plasmin System in Rheumatoid Arthritis. Arthritis & Rhematism. Sep. 2002;46(9):2268-79.

(Continued)

*Primary Examiner* — Brad Duffy
*Assistant Examiner* — Nelson B Moseley, II
(74) *Attorney, Agent, or Firm* — Wolf, Greenfield & Sacks, P.C.

(57) ABSTRACT

In some aspects, general methods to develop highly selective inhibitory antibodies towards members of the metzincin superfamily of metalloproteases and their application for therapeutic and diagnostic uses are provided. The methods employ the generation of novel catalytic cleft-directed antibodies with neutralizing selectivity for the targeted metzincin metalloendoproteinase employing immunogenic peptides encompassing the consensus metzincin catalytic motif. In some aspects, methods include the employment of such antibodies for therapeutic purposes and/or as an inhibitory component of an assay system allowing discrimination between the activity of the targeted metzincin and other endogenous metzincins within a biological sample. Such assays may be employed for diagnostic or prognostic purposes.

11 Claims, 1 Drawing Sheet

(56) References Cited

OTHER PUBLICATIONS

Carmeliet et al., Targeted deficiency or cytosolic truncation of the VE-cadherin gene in mice impairs VEGF-mediated endothelial survival and angiogenesis. Cell. Jul. 23, 1999;98(2):147-57.
Charrier et al., ADAM-15/metargidin mediates homotypic aggregation of human T lymphocytes and heterotypic interactions of T lymphocytes with intestinal epithelial cells. J Biol Chem. Jun. 8, 2007;282(23):16948-58.
Charrier-Hisamuddin et al.,. ADAM-15: a metalloprotease that mediates inflammation. FASEB J. Mar. 2008;22(3):641-53. Epub Sep. 28, 2007.
Chen et al., Akt1 regulates pathological angiogenesis, vascular maturation and permeability in vivo. Nat Med. Nov. 2005;11(11):1188-96. Epub Oct. 16, 2005.
Cirilli et al., 2 angstrom X-ray structure of adamalysin II complexed with a peptide phosphonate inhibitor adopting a retro-binding mode. FEBS Lett. Dec. 1, 1997;418(3):319-22.
Dance et al., The adaptor protein Gab1 couples the stimulation of vascular endothelial growth factor receptor-2 to the activation of phosphoinositide 3-kinase. J Biol Chem. Aug. 11, 2006;281(32):23285-95. Epub Jun. 20, 2006.
Davies et al., Microglia and macrophages are increased in response to ischemia-induced retinopathy in the mouse retina. Mol Vis. May 10, 2006;12:467-77.
Devy et al., New Strategies for the Next Generation of Matrix-Metalloproteinase Inhibitors: Selectively Targeting Membrane-Anchored MMPs with Therapeutic Antibodies. Biochem Res Int. 2011;2011:191670. doi: 10.1155/2011/191670. Epub Oct. 28, 2010.
Eto et al., RGD-independent binding of integrin alpha9beta1 to the ADAM-12 and -15 disintegrin domains mediates cell-cell interaction. J Biol Chem. Nov. 10, 2000;275(45):34922-30.
Fong et al., Role of the Flt-1 receptor tyrosine kinase in regulating the assembly of vascular endothelium. Nature. Jul. 6, 1995;376(6535):66-70.
Gerber et al., Vascular endothelial growth factor regulates endothelial cell survival through the phosphatidylinositol 3'-kinase/Akt signal transduction pathway. Requirement for Flk-1/KDR activation. J Biol Chem. Nov. 13, 1998;273(46):30336-43.
Gerhardt et al., VEGF guides angiogenic sprouting utilizing endothelial tip cell filopodia. J Cell Biol. Jun. 23, 2003;161(6):1163-77.
Gerhardt, How do endothelial cells orientate? EXS. 2005;(94):3-15.
Gomis-Rüth, Catalytic domain architecture of metzincin metalloproteases. J Biol Chem. Jun. 5, 2009;284(23):15353-7. doi: 10.1074/jbc.R800069200. Epub Feb. 5, 2009.
Ham et al., ADAM15 is an adherens junction molecule whose surface expression can be driven by VE-cadherin. Exp Cell Res. Oct. 1, 2002;279(2):239-47.
Herren et al., Expression of a disintegrin-like protein in cultured human vascular cells and in vivo. FASEB J. Feb. 1997;11(2):173-80.
Hiratsuka et al., Flt-1 lacking the tyrosine kinase domain is sufficient for normal development and angiogenesis in mice. Proc Natl Acad Sci U S A. Aug. 4, 1998;95(16):9349-54.
Horiuchi et al., Potential role for ADAM15 in pathological neovascularization in mice. Mol Cell Biol. Aug. 2003;23(16):5614-24.
Ikenoue et al., Functional analysis of PIK3CA gene mutations in human colorectal cancer. Cancer Res. Jun. 1, 2005;65(11):4562-7.
Jiang et al., Astrocytes modulate retinal vasculogenesis: effects on fibronectin expression. J Cell Sci. Sep. 1994;107 ( Pt 9):2499-508.
Krätzschmar et al., Metargidin, a membrane-anchored metalloprotease-disintegrin protein with an RGD integrin binding sequence. J Biol Chem. Mar. 1, 1996;271(9):4593-6.
Laramée et al., The scaffolding adapter Gab1 mediates vascular endothelial growth factor signaling and is required for endothelial cell migration and capillary formation. J Biol Chem. Mar. 16, 2007;282(11):7758-69. Epub Dec. 17, 2006.

Lee et al., PIK3CA gene is frequently mutated in breast carcinomas and hepatocellular carcinomas. Oncogene. Feb. 17, 2005;24(8):1477-80.
Levine et al., Frequent mutation of the PIK3CA gene in ovarian and breast cancers. Clin Cancer Res. Apr. 15, 2005;11(8):2875-8.
Lunn et al., Purification of ADAM 10 from bovine spleen as a TNFalpha convertase. FEBS Lett. Jan. 6, 1997;400(3):333-5.
Macri et al., Growth factor binding to the pericellular matrix and its importance in tissue engineering. Adv Drug Deliv Rev. Nov. 10, 2007;59(13):1366-81. Epub Aug. 16, 2007.
Mahabeleshwar et al., Integrin signaling is critical for pathological angiogenesis. J Exp Med. Oct. 30, 2006;203(11):2495-507. Epub Oct. 9, 2006.
Maretzky et al., Characterization of the catalytic activity of the membrane-anchored metalloproteinase ADAM15 in cell-based assays. Biochem J. Apr. 28, 2009;420(1):105-13.
Martin et al., The role of ADAM 15 in glomerular mesangial cell migration. J Biol Chem. Sep. 13, 2002;277(37):33683-9. Epub Jun. 28, 2002.
Matsumoto et al., VEGF receptor-2 Y951 signaling and a role for the adapter molecule TSAd in tumor angiogenesis. EMBO J. Jul. 6, 2005;24(13):2342-53. Epub Jun. 16, 2005.
McGeehan et al., Regulation of tumour necrosis factor-alpha processing by a metalloproteinase inhibitor. Nature. Aug. 18, 1994;370(6490):558-61.
Miralem et al., VEGF(165) requires extracellular matrix components to induce mitogenic effects and migratory response in breast cancer cells. Oncogene. Sep. 6, 2001;20(39):5511-24.
Murphy, Fell-Muir Lecture: Metalloproteinases: from demolition squad to master regulators. Int J Exp Pathol. 2010;91:303-13.
Murphy, The ADAMs: signalling scissors in the tumour microenvironment. Nat Rev Cancer. Dec. 2008;8(12):929-41. Epub Nov. 13, 2008.
Najy, et al.; "ADAM15 Supports Prostate Cancer Metastasis by Modulating Tumor Cell—Endothelial Cell Interaction"; Cancer Res (2008); 68(4): 1092-1099.
Nath et al., Interaction of metargidin (ADAM-15) with alphavbeta3 and alpha5beta1 integrins on different haemopoietic cells. J Cell Sci. Feb. 1999;112 (Pt 4):579-87.
Pan et al., Kuzbanian controls proteolytic processing of Notch and mediates lateral inhibition during *Drosophila* and vertebrate neurogenesis. Cell. Jul. 25, 1997;90(2):271-80.
Poghosyan et al., Phosphorylation-dependent interactions between ADAM15 cytoplasmic domain and Src family protein-tyrosine kinases. J Biol Chem. Feb. 15, 2002;277(7):4999-5007. Epub Dec. 10, 2001.
Prager et al., Vascular endothelial growth factor (VEGF) induces rapid prourokinase (pro-uPA) activation on the surface of endothelial cells. Blood. Feb. 1, 2004;103(3):955-62. Epub Oct. 2, 2003.
Prager et al., Vascular endothelial growth factor receptor-2-induced initial endothelial cell migration depends on the presence of the urokinase receptor. Circ Res. Jun. 25, 2004;94(12):1562-70. Epub May 6, 2004.
Primo et al., Essential role of PDK1 in regulating endothelial cell migration. J Cell Biol. Mar. 26, 2007;176(7):1035-47. Epub Mar. 19, 2007.
Qi et al., Phosphoinositide 3 kinase is critical for survival, mitogenesis and migration but not for differentiation of endothelial cells. Angiogenesis. 1999;3(4):371-80.
Qiu et al., PIK3CA mutations in head and neck squamous cell carcinoma. Clin Cancer Res. Mar. 1, 2006;12(5):1441-6.
Rahman et al., Novel hepatocyte growth factor (HGF) binding domains on fibronectin and vitronectin coordinate a distinct and amplified Met-integrin induced signalling pathway in endothelial cells. BMC Cell Biol. Feb. 17, 2005;6(1):8.
Rahman et al., Adam 15 is a negative regulator of endothelial cell migration induced by VEGF-Firbronectin. Presented at "Fibronectin, Integrins and Related Molecules" Gordon Research Conference. Jan. 30-Feb. 4, 2005. 8 slides.
Rahman et al., Adam 15 is essential for regulated angiogenesis and vegf signalling to akt through proteolytic processing of the uroki-

(56) References Cited

OTHER PUBLICATIONS nase-type plasminogen activator receptor (upar). British Society for Cardiovascular Research Spring Meeting 2007. Abstract No. 003. 2 pages.

Roy, et al.; "Making the cut: Protease-mediated regulation of angiogenesis"; Experimental Cell Research (2006); 312: 608-622.

Ruhrberg et al., Spatially restricted patterning cues provided by heparin-binding VEGF-A control blood vessel branching morphogenesis. Genes Dev.Oct. 15, 2002;16(20):2684-98.

Saal et al., PIK3CA mutations correlate with hormone receptors, node metastasis, and ERBB2, and are mutually exclusive with PTEN loss in human breast carcinoma. Cancer Res. Apr. 1, 2005;65(7):2554-9.

Samuels et al., High frequency of mutations of the PIK3CA gene in human cancers.Science. Apr. 23, 2004;304(5670):554. Epub Mar. 11, 2004.

Samuels et al., Mutant PIK3CA promotes cell growth and invasion of human cancer cells. Cancer Cell. Jun. 2005;7(6):561-73.

Saunders et al., Coregulation of vascular tube stabilization by endothelial cell TIMP-2 and pericyte TIMP-3. J Cell Biol. Oct. 9, 2006;175(1):179-91.

Saunders et al., MMP-1 activation by serine proteases and MMP-10 induces human capillary tubular network collapse and regression in 3D collagen matrices. J Cell Sci. May 15, 2005;118(Pt 10):2325-40. Epub May 3, 2005.

Seals et al., The ADAMs family of metalloproteases: multidomain proteins with multiple functions. Genes Dev. Jan. 1, 2003;17(1):7-30.

Sela-Passwell et al., New opportunities in drug design of metalloproteinase inhibitors: combination between structure-function experimental approaches and systems biology. Expert Opin Drug Discov. May 2011;6(5):527-42. doi: 10.1517/17460441.2011.560936. Epub Apr. 21, 2011.

Stalmans et al., Arteriolar and venular patterning in retinas of mice selectively expressing VEGF isoforms. J Clin Invest. Feb. 2002;109(3):327-36.

Takahashi et al., The 230 kDa mature form of KDR/Flk-1 (VEGF receptor-2) activates the PLC-gamma pathway and partially induces mitotic signals in NIH3T3 fibroblasts. Oncogene. May 1, 1997;14(17):2079-89.

Tape et al., Cross-domain inhibition of TACE ectodomain. Proc Natl Acad Sci U S A. Apr. 5, 2011;108(14):5578-83. doi: 10.1073/pnas.1017067108. Epub Mar. 17, 2011.

Trochon et al., Endothelial metalloprotease-disintegrin protein (ADAM) is implicated in angiogenesis in vitro. Angiogenesis. 1998;2(3):277-85.

Uemura et al., Tlx acts as a proangiogenic switch by regulating extracellular assembly of fibronectin matrices in retinal astrocytes. J Clin Invest. Feb. 2006;116(2):369-77. Epub Jan. 19, 2006.

White, ADAMs: modulators of cell-cell and cell-matrix interactions. Curr Opin Cell Biol. Oct. 2003;15(5):598-606.

Wijelath et al., Fibronectin promotes VEGF-induced CD34 cell differentiation into endothelial cells. J Vasc Surg. Mar. 2004;39(3):655-60.

Wijelath et al., Heparin-II domain of fibronectin is a vascular endothelial growth factor-binding domain: enhancement of VEGF biological activity by a singular growth factor/matrix protein synergism. Circ Res. Oct. 13, 2006;99(8):853-60. Epub Sep. 28, 2006.

Wijelath et al., Novel vascular endothelial growth factor binding domains of fibronectin enhance vascular endothelial growth factor biological activity. Circ Res. Jul. 12, 2002;91(1):25-31.

Yamaoka-Tojo et al., IQGAP1 mediates VE-cadherin-based cell-cell contacts and VEGF signaling at adherence junctions linked to angiogenesis. Arterioscler Thromb Vasc Biol. Sep. 2006;26(9):1991-7. Epub Jun. 8, 2006.

Yang et al., The ADAMs family: coordinators of nervous system development, plasticity and repair. Prog Neurobiol. Jun. 2006;79(2):73-94. Epub Jul. 7, 2006.

Zhang et al., Extracellular matrix regulates endothelial functions through interaction of VEGFR-3 and integrin alpha5beta1. J Cell Physiol. Jan. 2005;202(1):205-14.

Zhang et al., Specific interaction of the recombinant disintegrin-like domain of MDC-15 (metargidin, ADAM-15) with integrin alphavbeta3. J Biol Chem. Mar. 27, 1998;273(13):7345-50.

\* cited by examiner

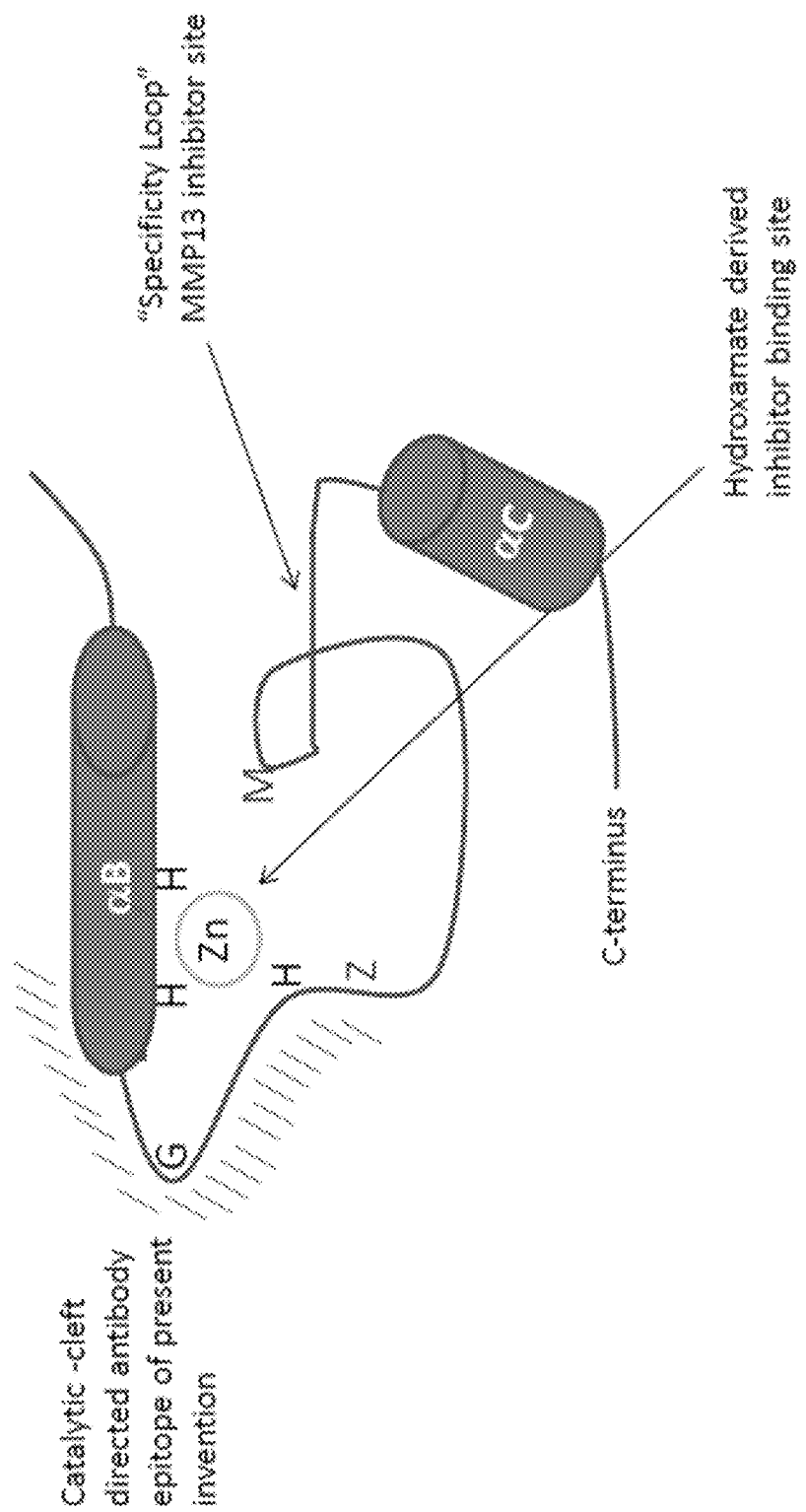

SEQUENCE LISTING

```
<160> NUMBER OF SEQ ID NOS: 71

<210> SEQ ID NO 1
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(4)
<223> OTHER INFORMATION: Xaa denotes any amino acid
<220> FEATURE:
<221> NAME/KEY: misc_feature
<222> LOCATION: (6)..(7)
<223> OTHER INFORMATION: Xaa denotes any amino acid
<220> FEATURE:
<221> NAME/KEY: misc_feature
<222> LOCATION: (9)..(10)
<223> OTHER INFORMATION: Xaa denotes any amino acid

<400> SEQUENCE: 1

His Glu Xaa Xaa His Xaa Xaa Gly Xaa Xaa His
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(4)
<223> OTHER INFORMATION: Xaa denotes any amino acid
<220> FEATURE:
<221> NAME/KEY: misc_feature
<222> LOCATION: (6)..(7)
<223> OTHER INFORMATION: Xaa denotes any amino acid
<220> FEATURE:
<221> NAME/KEY: misc_feature
<222> LOCATION: (9)..(10)
<223> OTHER INFORMATION: Xaa denotes any amino acid

<400> SEQUENCE: 2

His Glu Xaa Xaa His Xaa Xaa Gly Xaa Xaa Asp
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa denotes a variable bulky hydrophobic or
      non-polar residue
<220> FEATURE:
<221> NAME/KEY: misc_feature
```

```
<222> LOCATION: (4)..(4)
<223> OTHER INFORMATION: Xaa denotes any amino acid
<220> FEATURE:
<221> NAME/KEY: misc_feature
<222> LOCATION: (6)..(6)
<223> OTHER INFORMATION: Xaa denotes any amino acid
<220> FEATURE:
<221> NAME/KEY: misc_feature
<222> LOCATION: (7)..(7)
<223> OTHER INFORMATION: Xaa denotes a variable bulky hydrophobic or
      non-polar residue
<220> FEATURE:
<221> NAME/KEY: misc_feature
<222> LOCATION: (9)..(9)
<223> OTHER INFORMATION: Xaa denotes a variable bulky hydrophobic or
      non-polar residue
<220> FEATURE:
<221> NAME/KEY: misc_feature
<222> LOCATION: (10)..(10)
<223> OTHER INFORMATION: Xaa denotes any amino acid
<220> FEATURE:
<221> NAME/KEY: misc_feature
<222> LOCATION: (12)..(12)
<223> OTHER INFORMATION: Xaa denotes a subfamily specific residue

<400> SEQUENCE: 3

His Glu Xaa Xaa His Xaa Xaa Gly Xaa Xaa His Xaa
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa denotes a variable bulky hydrophobic or
      non-polar residue
<220> FEATURE:
<221> NAME/KEY: misc_feature
<222> LOCATION: (4)..(4)
<223> OTHER INFORMATION: Xaa denotes any amino acid
<220> FEATURE:
<221> NAME/KEY: misc_feature
<222> LOCATION: (6)..(6)
<223> OTHER INFORMATION: Xaa denotes any amino acid
<220> FEATURE:
<221> NAME/KEY: misc_feature
<222> LOCATION: (7)..(7)
<223> OTHER INFORMATION: Xaa denotes a variable bulky hydrophobic or
      non-polar residue
<220> FEATURE:
<221> NAME/KEY: misc_feature
<222> LOCATION: (9)..(9)
<223> OTHER INFORMATION: Xaa denotes a variable bulky hydrophobic or
      non-polar residue
<220> FEATURE:
<221> NAME/KEY: misc_feature
<222> LOCATION: (10)..(10)
<223> OTHER INFORMATION: Xaa denotes any amino acid
<220> FEATURE:
<221> NAME/KEY: misc_feature
<222> LOCATION: (12)..(12)
<223> OTHER INFORMATION: Xaa denotes a subfamily specific residue

<400> SEQUENCE: 4

His Glu Xaa Xaa His Xaa Xaa Gly Xaa Xaa Asp Xaa
1               5                   10

<210> SEQ ID NO 5
<211> LENGTH: 8
<212> TYPE: PRT
<213> ORGANISM: Artificial Sequence
```

-continued

```
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa denotes any amino acid
<220> FEATURE:
<221> NAME/KEY: misc_feature
<222> LOCATION: (3)..(3)
<223> OTHER INFORMATION: Xaa denotes a variable bulky hydrophobic or
      non-polar residue
<220> FEATURE:
<221> NAME/KEY: misc_feature
<222> LOCATION: (5)..(5)
<223> OTHER INFORMATION: Xaa denotes a variable bulky hydrophobic or
      non-polar residue
<220> FEATURE:
<221> NAME/KEY: misc_feature
<222> LOCATION: (6)..(6)
<223> OTHER INFORMATION: Xaa denotes any amino acid
<220> FEATURE:
<221> NAME/KEY: misc_feature
<222> LOCATION: (8)..(8)
<223> OTHER INFORMATION: Xaa denotes a subfamily specific residue

<400> SEQUENCE: 5

His Xaa Xaa Gly Xaa Xaa His Xaa
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa denotes any amino acid
<220> FEATURE:
<221> NAME/KEY: misc_feature
<222> LOCATION: (3)..(3)
<223> OTHER INFORMATION: Xaa denotes a variable bulky hydrophobic or
      non-polar residue
<220> FEATURE:
<221> NAME/KEY: misc_feature
<222> LOCATION: (5)..(5)
<223> OTHER INFORMATION: Xaa denotes a variable bulky hydrophobic or
      non-polar residue
<220> FEATURE:
<221> NAME/KEY: misc_feature
<222> LOCATION: (6)..(6)
<223> OTHER INFORMATION: Xaa denotes any amino acid
<220> FEATURE:
<221> NAME/KEY: misc_feature
<222> LOCATION: (8)..(8)
<223> OTHER INFORMATION: Xaa denotes a subfamily specific residue

<400> SEQUENCE: 6

His Xaa Xaa Gly Xaa Xaa Asp Xaa
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 7

Ile Ala His Glu Leu Gly His Ser Leu Gly Leu Asp His Asp
1               5                   10
```

```
<210> SEQ ID NO 8
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 8

His Ser Leu Gly Leu Asp His Asp
1               5

<210> SEQ ID NO 9
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 9

Met Ala His Glu Met Gly His Asn Leu Gly Met Asp His Asp
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 10

Leu Ala His Glu Leu Gly His Asn Phe Gly Met Asn His Asp
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 11

Thr Thr His Glu Leu Gly His Asn Phe Gly Ala Glu His Asp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 12

Phe Ala His Glu Val Gly His Asn Phe Gly Ser Pro His Asp
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 13

Met Ala His Gln Leu Gly His Asn Leu Gly Met Gln His Asp
1               5                   10

<210> SEQ ID NO 14
```

<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 14

Val Ala His Glu Leu Gly His Asn Leu Gly Met Asn His Asp
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 15

Met Ala His Glu Met Gly His Asn Phe Gly Met Thr His Asp
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 16

Met Ala His Glu Met Gly His Asn Phe Gly Met Phe His Asp
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 17

Met Ala His Glu Ile Gly His Ser Leu Gly Leu Ser His Asp
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 18

Val Ala His Glu Thr Gly His Val Leu Gly Met Glu His Asp
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 19

Ala Ala His Glu Leu Gly His Val Phe Asn Met Leu His Asp
1               5                   10

<210> SEQ ID NO 20
<211> LENGTH: 14

```
<212> TYPE: PRT
<213> ORGANISM: Artificial Sequence
<220> FEATURE:
<223> OTHER INFORMATION: Synthetic Polypeptide

<400> SEQUENCE: 20

Val Ala His Glu Ile Gly His Leu Leu Gly Leu Ser His Asp
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 21

Val Ala His Glu Leu Gly His Ser Phe Gly Ile Gln His Asp
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 22

Ile Ala His Glu Thr Gly His Val Leu Gly Met Glu His Asp
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 23

Ala Ala His Glu Leu Gly His Ser Leu Gly Leu Ser His Ser
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 24

Ala Ala His Glu Phe Gly His Ala Leu Gly Ile Asp His Ser
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 25

Ala Ala His Glu Ile Gly His Ser Leu Gly Leu Phe His Ser
1               5                   10

<210> SEQ ID NO 26
<211> LENGTH: 14
<212> TYPE: PRT
```

```
<213> ORGANISM: Artificial Sequence
<220> FEATURE:
<223> OTHER INFORMATION: Synthetic Polypeptide

<400> SEQUENCE: 26

Ala Ala His Glu Phe Gly His Ala Met Gly Ile Glu His Ser
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 27

Ala Thr His Glu Leu Gly His Ser Leu Gly Met Gly His Ser
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 28

Ala Ala His Glu Leu Gly His Ser Leu Gly Leu Phe His Ser
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 29

Ala Ala His Glu Phe Gly His Val Leu Gly Leu Gln His Thr
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 30

Ala Val His Glu Ile Gly His Ser Leu Gly Leu Gly His Ser
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 31

Ala Ala His Glu Phe Gly His Ser Leu Gly Leu Asp His Ser
1               5                   10

<210> SEQ ID NO 32
<211> LENGTH: 14
<212> TYPE: PRT
<213> ORGANISM: Artificial Sequence
```

```
<220> FEATURE:
<223> OTHER INFORMATION: Synthetic Polypeptide

<400> SEQUENCE: 32

Ala Ala His Glu Val Gly His Ala Leu Gly Leu Gly His Ser
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 33

Ala Val His Glu Leu Gly His Ala Leu Gly Leu Glu His Ser
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 34

Ala Val His Glu Leu Gly His Ala Leu Gly Leu Glu His Ser
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 35

Ala Val His Glu Leu Gly His Ala Leu Gly Leu Glu His Ser
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 36

Ala Val His Glu Phe Gly His Ala Leu Gly Leu Gly His Ser
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 37

Val Gln His Glu Phe Leu His Ala Leu Gly Phe Trp His Glu
1               5                   10

<210> SEQ ID NO 38
<211> LENGTH: 14
<212> TYPE: PRT
<213> ORGANISM: Artificial Sequence
<220> FEATURE:
```

<223> OTHER INFORMATION: Synthetic Polypeptide

<400> SEQUENCE: 38

Ile Glu His Glu Ile Leu His Ala Leu Gly Phe Tyr His Glu
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 39

Val Val His Glu Leu Gly His Val Val Gly Phe Trp His Glu
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 40

Val Val His Glu Leu Gly His Val Ile Gly Phe Trp His Glu
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(2)
<223> OTHER INFORMATION: Xaa denotes any amino acid
<220> FEATURE:
<221> NAME/KEY: misc_feature
<222> LOCATION: (5)..(5)
<223> OTHER INFORMATION: Xaa denotes a variable bulky hydrophobic or
      non-polar residue
<220> FEATURE:
<221> NAME/KEY: misc_feature
<222> LOCATION: (6)..(6)
<223> OTHER INFORMATION: Xaa denotes any amino acid
<220> FEATURE:
<221> NAME/KEY: misc_feature
<222> LOCATION: (8)..(8)
<223> OTHER INFORMATION: Xaa denotes any amino acid
<220> FEATURE:
<221> NAME/KEY: misc_feature
<222> LOCATION: (9)..(9)
<223> OTHER INFORMATION: Xaa denotes a variable bulky hydrophobic or
      non-polar residue
<220> FEATURE:
<221> NAME/KEY: misc_feature
<222> LOCATION: (11)..(11)
<223> OTHER INFORMATION: Xaa denotes a variable bulky hydrophobic or
      non-polar residue
<220> FEATURE:
<221> NAME/KEY: misc_feature
<222> LOCATION: (12)..(12)
<223> OTHER INFORMATION: Xaa denotes any amino acid
<220> FEATURE:
<221> NAME/KEY: misc_feature
<222> LOCATION: (14)..(14)
<223> OTHER INFORMATION: Xaa denotes a subfamily specific residue

<400> SEQUENCE: 41

Xaa Xaa His Glu Xaa Xaa His Xaa Xaa Gly Xaa Xaa His Xaa

```
<210> SEQ ID NO 42
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 42

His Asn Leu Gly Met Asp His Asp
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 43

His Asn Phe Gly Met Asn His Asp
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 44

His Asn Phe Gly Ala Glu His Asp
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 45

His Asn Phe Gly Ser Pro His Asp
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 46

His Asn Leu Gly Met Gln His Asp
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 47

His Asn Leu Gly Met Asn His Asp
1               5
```

```
<210> SEQ ID NO 48
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 48

His Asn Phe Gly Met Thr His Asp
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 49

His Asn Phe Gly Met Phe His Asp
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 50

His Ser Leu Gly Leu Ser His Asp
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 51

His Val Leu Gly Met Glu His Asp
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 52

His Val Phe Asn Met Leu His Asp
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 53

His Leu Leu Gly Leu Ser His Asp
1               5
```

```
<210> SEQ ID NO 54
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 54

His Ser Phe Gly Ile Gln His Asp
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 55

His Val Leu Gly Met Glu His Asp
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 56

His Ser Leu Gly Leu Ser His Ser
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 57

His Ala Leu Gly Ile Asp His Ser
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 58

His Ser Leu Gly Leu Phe His Ser
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 59

His Ala Met Gly Ile Glu His Ser
1               5
```

```
<210> SEQ ID NO 60
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 60

His Ser Leu Gly Met Gly His Ser
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 61

His Ser Leu Gly Leu Phe His Ser
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 62

His Val Leu Gly Leu Gln His Thr
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 63

His Ser Leu Gly Leu Gly His Ser
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 64

His Ser Leu Gly Leu Asp His Ser
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 65

His Ala Leu Gly Leu Gly His Ser
1               5

<210> SEQ ID NO 66
```

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 66

His Ala Leu Gly Leu Glu His Ser
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 67

His Ala Leu Gly Leu Gly His Ser
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 68

His Ala Leu Gly Phe Trp His Glu
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 69

His Ala Leu Gly Phe Tyr His Glu
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 70

His Val Val Gly Phe Trp His Glu
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 71

His Val Ile Gly Phe Trp His Glu
1               5
```

METHODS FOR THE DEVELOPMENT OF METZINCIN-SELECTIVE CATALYTIC CLEFT DIRECTED ANTIBODIES FOR THERAPEUTIC AND DIAGNOSTIC APPLICATIONS

RELATED APPLICATIONS

This application is a national stage filing under 35 U.S.C. §371 of international PCT application PCT/IB2011/002860, filed Oct. 1, 2011, which was published under PCT Article 21(2) in English and claims the benefit under 35 U.S.C. 119(e) of U.S. provisional patent application Ser. No. 61/389,176, filed Oct. 1, 2010, the contents of which are incorporated herein by reference in their entirety.

FIELD OF INVENTION

Aspects of the present invention relate to methods of measuring metzincin metalloendoproteinase activity, developing inhibitory antibodies and antigen binding fragments thereof, immunogenic peptides and epitopes therein, synthetic peptide substrates for metalloendoproteinases and methods of detection of catalysis.

BACKGROUND OF THE INVENTION

The progression of many dilapidating diseases such as cancer, rheumatoid arthritis and cardiovascular disease are characterised by the involvement of several subclasses of the metalloendoproteinase superfamily termed metzincins (1, 2). Both MMPs (matrix metalloproteinases-subclass matrixins) and ADAMs (a disintegrin and metalloprotease-subclass reprolysins) have an established role in cancer progression, the retinopathies and inflammatory pathologies such as inflammatory bowel disease, arthritis and Crohn's. Other metzincins including the meprins are associated with renal and urinary tract pathologies and the pappalysins with pregnancy-related hypertensive disorders (see below). Accordingly, there is a need for methods and compositions for determining levels of different metzincins in a biological sample and to inhibit therapeutically the catalytic activity of particular metzincins associated with the progression of the above mentioned pathologies.

SUMMARY

In some embodiments, aspects of the invention relate to methods and compositions for inhibiting, e.g., specifically inhibiting, one or more members of the metzincin family of proteases. Inhibiting, e.g., specifically, one or more metzincin protease(s) can be useful in therapy to treat conditions associated with high levels of activity (e.g., due to overexpression) of one or more metzincin proteases. Inhibiting, e.g., specifically, one or more metzincin protease(s) can be useful in an assay to evaluate the relative activity of one or more metzincin proteases.

In some embodiments, an antibody is raised against a peptide that includes at least an epitope from the catalytic cleft of a metzincin protease. In some embodiments, an epitope of the catalytic cleft consists of or includes the C-terminal 6, 7, or 8 amino acids of any of the peptides shown in Table 3, or of the corresponding consensus sequence, or of a corresponding sequence of a related protease. In some embodiments, one or more of these epitopes is provided as part of a longer peptide (e.g., an about 10-20 amino acid peptide, an about 15 amino acid peptide, or other immunogenic peptide). Accordingly, the 6-8 amino acid epitope may be provided along with several (e.g., 1-5, 1-10, or more) N-terminal and/or C-terminal amino acids. In some embodiments, these may correspond to the N-terminal and/or C-terminal amino acids of the corresponding protease. However, in some embodiments, these may be other sequences (e.g., from a different protease, or of another sequence that is known to have one or more desired structural and/or immunogenic properties). In some embodiments, an N-terminal peptide that has alpha-helical properties is added. In some embodiments, a C-terminal peptide corresponding to the C-terminal sequence of the same protease as the epitope is used (e.g., to provide further specificity). In some embodiments, this additional C-terminal peptide is 1-5 amino acids long. In some embodiments, this additional C-terminal peptide does not include the conserved methionine (Met) of the Met-turn. Accordingly, in some embodiments, a minimal peptide epitope is used alone as an immunogen. In some embodiments, the minimal peptide could have one or more additional amino acids (e.g., 1-5, 5-10, or more) at its N-terminal and/or C-terminal ends to be used as an immunogen. In some embodiments, the additional amino acids be the corresponding amino acids of a metzincin protease of interest. In some embodiments, the additional amino acids can be generic amino acids (e.g., not protease-specific) that are used to provide structure and/or stabilize the peptide for effective immunization.

Accordingly, in some embodiments, any one or more peptides of Table 3 may be used to generate antibodies and/or to administer to a subject. In some embodiments, the C-terminal 8 amino acids of any peptide of Table 3 may be used (e.g., HNLGMDHD (SEQ ID NO: 42), HNFGMNHD (SEQ ID NO: 43), HNFGAEHD (SEQ ID NO: 44), HNFGSPHD (SEQ ID NO: 45), HNLGMQHD (SEQ ID NO: 46), HNLGMNHD (SEQ ID NO: 47), HNFGMTHD (SEQ ID NO: 48), HNFGMFHD (SEQ ID NO: 49), HSLGLSHD (SEQ ID NO: 50), HVLGMEHD (SEQ ID NO: 51), HVFNMLHD (SEQ ID NO: 52), HLLGLSHD (SEQ ID NO: 53), HSFGIQHD (SEQ ID NO: 54), HVLGMEHD (SEQ ID NO: 55), HSLGLSHS (SEQ ID NO: 56), HALGIDHS (SEQ ID NO: 57), HSLGLFHS (SEQ ID NO: 58), HAMGIEHS (SEQ ID NO: 59), HSLGMGHS (SEQ ID NO: 60), HSLGLFHS (SEQ ID NO: 61), HVLGLQHT (SEQ ID NO: 62), HSLGLGHS (SEQ ID NO: 63), HSLGLDHS (SEQ ID NO: 64), HALGLGHS (SEQ ID NO: 65), HALGLEHS (SEQ ID NO: 66), HALGLGHS (SEQ ID NO: 67), HALGFWHE (SEQ ID NO: 68), HALGFYHE (SEQ ID NO: 69), HVVGFWHE (SEQ ID NO: 70), HVIGFWHE (SEQ ID NO: 71), or any combination thereof). In some embodiments, one or more of the peptides (e.g., of Table 3, or the C-terminal 6, 7, or 8 amino acids of these peptides) may also have an additional 1-5 (e.g., 1, 2, 3, 4, or 5) amino acids from the corresponding protease, and optionally additional N-terminal and/or C-terminal (e.g., protease specific or non-protease specific) to provide additional structural properties if appropriate.

In some embodiments, the peptides described herein can be used as immunogens to generate antibodies (e.g., in animal systems) that are useful (e.g., in therapy and/or for assays as described herein).

In some embodiments, the peptides described herein can be used as therapeutic immunogens that can be administered to a subject (e.g., a human subject) in order to stimulate the production of subject antibodies that may be useful to reduce the level of one or more proteases in a subject that suffers from a condition associated with an excessive level of the protease(s).

It should be appreciated that the peptides may be administered alone or in combination with one or more suitable adjuvants and/or other factors. In some embodiments, a monoclonal antibody composition may be generated. In some embodiments, a polyclonal antibody composition may be generated. In some embodiments, a single type of peptide may be used to generate antibodies. In some embodiments, a mixture of peptides may be used (for example to generate a polyclonal composition of antibodies against a plurality of different metzincin proteases.

It should be appreciated that any suitable technique may be used for preparing (e.g., by isolating and/or synthesizing) one or more peptides and/or antibodies described herein.

Accordingly, in some embodiments aspects of the invention relate to a method of producing an antibody or antigen-binding fragment thereof that specifically inactivates a metzincin protease, includes raising an antibody against a composition comprising an metzincin-protease-specific epitope. In some embodiments, the antibody is raised by immunizing a host animal with the epitope. In some embodiments, the antibody is raised in vitro (e.g., using phage display, bacterial display, yeast display, mammalian cell display, ribosome display or other library-based recombinant platforms).

In some embodiments, an epitope consists of or comprises one of the following peptides:

```
HXBGBXHZ        (SEQ ID NO: 5)

HXBGBXDZ        (SEQ ID NO: 6)
``` wherein, X denotes any amino acid, B denotes a variable bulky hydrophobic or non-polar residue (e.g. I, L, F, M, Y, V etc.) and Z denotes the subfamily specific residue referred to herein.

In some embodiments, an epitope consists of or comprises a peptide selected from the epitopes and/or full peptides shown in Table 3. In some embodiments, the epitope is not an ADAM 15 peptide.

In some embodiments, aspects of the invention relate to an antibody that specifically inactivates a member of the metzincin protease family. In some embodiments the antibody completely inactivates the protease. In some embodiments, the antibody partially inactivates (e.g., by about 10%, about 10-25%, about 25-50%, about 50%, about 50-75%, about 75-90%, about 90%, about 95%, or more of less (for example in an in vitro assay or in a cell-based assay where the ratio of antibody to protease concentration is between about 10:1 and about 1:1, or in any other suitable assay described herein or known in the art). In some embodiments, the antibody does not specifically bind to or inactivate an ADAM 15 protease.

In some embodiments, aspects of the invention relate to a method of reducing the activity of a metzincin protease in subject by administering an antibody or antigen-binding fragment thereof to a subject, wherein the antibody specifically reduces the activity of a metzincin protease. In some embodiments, aspects of the invention relate to a method of reducing the activity of a metzincin protease in subject by contacting a cell or tissue with an antibody or antigen-binding fragment thereof to a subject, wherein the antibody specifically reduces the activity of a metzincin protease.

In some embodiments, aspects of the invention relate to a method of producing a specific anti-metzincin antibody response in a subject, the method comprising immunizing the subject with an epitope described herein. In some embodiments, the epitope is not an ADAM 15 peptide.

In some embodiments, aspects of the invention relate to a method of determining the activity of a metzincin protease in a biological sample, by contacting a biological sample with a metzincin substrate (e.g., a quenched fluorescent peptide that is a substrate for one or more metzincin proteases, for example one or more peptides described in ref. 30, the peptides and assay conditions of which are incorporated herein by reference) and a specific anti-metzincin antibody, and comparing the level of protease activity in the biological sample in the presence of the specific anti-metzincin antibody to the level of protease activity in the biological sample in the absence of the specific anti-metzincin antibody.

Accordingly, in some embodiments, aspects of the invention relate to methods for developing selective, catalysis-inhibiting antibodies to members of the metzincin superfamily of metalloproteases employing a catalytic cleft peptide encompassing one of the regions described herein as an immunogen.

In some embodiments, aspects of the invention relate to methods for treating a patient with a disease in which a single or multiple target metzincins promote disease progression by administering to said patient a therapeutic dose of a single metzincin selective, catalytic-cleft directed antibody or a combination of metzincin-selective catalytic cleft directed antibodies.

In some embodiments, aspects of the invention relate to methods of measuring the catalytic activity of a target metalloendoproteinase of the metzincin superfamily or subfamily thereof within a biological sample by the addition of inhibitory antibodies with specificity for the catalytic cleft of the target metzincin, thereby allowing the determination of the activity of the target metzincin by subtraction from an uninhibited sample. In some embodiments, aspects of the invention relate to one or more peptide immunogens encompassing but not restricted to a sequence corresponding to the consensus zinc binding motif of the metzincins described herein, optionally having a number not greater than five amino acid residues or coupling groups flanking the said sequence. In some embodiments, aspects of the invention relate to one or more antibodies that selectively inhibit a member of the metzincin protease family or subfamily. In some embodiments, the antibody selectively binds to a protease-specific epitope within the catalytic cleft region of the protease. In some embodiments, aspects of the invention relate to methods for determining the amount or activity of a metzincin protease in a sample, by contacting a sample with an antibody that selectively inhibits a metzincin protease, determining the level of protease activity in the sample relative to a control sample, thereby to determine the amount of activity of the metzincin protease in the sample. In some embodiments, the control sample is contacted with a different antibody. In some embodiments, the control sample is not contacted with an antibody. In some embodiments, the sample is a biological sample (e.g., a biological cell, tissue, fluid, or other sample, for example from a patient, or from another source).

It should be appreciated that the protease specific epitopes described herein also may be used as targets to generate other (e.g., non-antibody) specific binding agents (e.g., other protein or nucleic acid binding agents, for example aptamers and/or darpins). Such agents also may be used in therapy to treat protease-specific conditions as described herein for the antibodies. In some embodiments, one or more different types of specific binding agents may be used alone or together in any suitable combination.

These and other aspects of the inventions are described in more detail herein and in the attached FIGURE.

BRIEF DESCRIPTION OF THE DRAWING

FIG. 1 is a non-limiting diagrammatic representation of the general features of a metzincin catalytic cleft and C-terminal domain.

DETAILED DESCRIPTION

In some embodiments, aspects of the invention relate to methods and compositions for specifically inactivating and/or detecting particular metzincins in a biological sample. Currently, known metalloendoproteinase inhibitors are non-specific and cannot be used to distinguish between and/or specifically inactivate different metzincins that are in a biological sample. In contrast, Applicants have identified methods and techniques for developing binding agents (e.g., antibodies) that can specifically bind to and/or inactivate individual metalloproteases belonging to the metzincin superfamily and/or a subfamily thereof without affecting other members of the superfamily or subfamily.

In some embodiments, specific binding agents can be used to evaluate a biological sample to determine which metzincin metalloendoproteinases are present and/or active in the sample. In some embodiments, the level of activity of specific metzincins can be determined.

In certain embodiments, specific binding agents can be used to specifically inactivate one or more metzincins in vitro and/or in vivo. In some embodiments, subjects can be treated therapeutically by administering one or more specific binding agents to reduce the level of activity of particular metzincin(s) in the subject. For example, particular conditions associated with excessive metzincin activity can be treated by specifically inactivating one or more members of the metzincin family. In some embodiments one or more of the following proteases may be specifically inactivated to treat an associated disease. By way of example, there is strong evidence for involvement of members of the MMPs and ADAMs/ADAM-TS family in cancer progression most notably MMPs-1, -2-7, 9, and 14 and ADAMs 9,10,12,15, 17, and 19 (see discussion herein, Table 1, and refs, 3 and 4).

TABLE 1

Metzincin Therapeutic Targets and Disease Areas

| Human Pathology/ Process | ADAMs/ ADAM-TS | MMPs | Astacin | Pappalysin |
|---|---|---|---|---|
| Cancer-Tumour Progression & Angiogenesis | ADAM 8 | MMP1 | | |
| | ADAM 9 | MMP2 | | |
| | ADAM 10 | MMP7 | | |
| | ADAM 12 | MMP9 | | |
| | ADAM 15 | MMP10 | | |
| | ADAM 17 | MMP11 | | |
| | ADAM 19 | MMP12 | | |
| | ADAM 28 | MMP19 | | |
| | ADAM-TS | MT1-MMP (MMP14) | | |
| | ADAM TS-4 | MT2-MMP | | |
| | ADAM TS-5 | MT5-MMP | | |
| | | MT6-MMP | | |
| Inflammatory pathologies | ADAM 8 | | | |
| | ADAM 15 | MMP3 | | |
| | ADAM 17 | MMP13 | | |

TABLE 1-continued

Metzincin Therapeutic Targets and Disease Areas

| Human Pathology/ Process | ADAMs/ ADAM-TS | MMPs | Astacin | Pappalysin |
|---|---|---|---|---|
| | ADAM TS-2 | | | |
| | ADAMTS-14 | | | |
| Cardiovascular Disease | ADAM 15 | MMP-1 | | |
| | ADAM 17 | MMP-2 | | |
| | ADAM TS-7 | MMP-9 | | |
| Asthma | ADAM 33 | | | |
| Coagulatory | ADAM TS-13 | | | |
| Renal failure & urinary tract infections | | | Meprin 1A Meprin 1B | |
| Pulmonary Destruction | | MMP12 (MMPE) | | |
| Pre-eclampsia | | | | Pappalysin-A |

It also should be appreciated that one or more binding agents of the invention may be used therapeutically alone or in combination with one or more other therapeutic agents.

Aspects of the invention are based, at least in part, on the identification of particular epitopes of the metzincin family of proteases that can be used to raise antibodies having specific inactivating properties. Remarkably, epitopes within the catalytic cleft can be used to raise antibodies that i) bind specifically to individual protease members of the metzincin superfamily and/or ii) specifically inactivate individual protease members of the metzincin superfamily.

Accordingly, an antibody or antigen-binding fragment thereof that is specific for a particular metzincin protease (or group of proteases) can be used to treat a condition associated with abnormally high levels (e.g., due to overexpression and/or unregulated expression) of that protease (or group of proteases).

Antibody affinities can range from low-picomolar to high nanomolar, e.g., Kd's between 50 pM to 500 nM, but it is expected that antibodies described herein will be in the range of 0.1 nM-50 nM. IC50 values in cell based assays can range from 0.5 to 500 nM, and are likely to fall in the range of 10 nM-200 nM. In some embodiments, based upon the observations with ADAM 15 antibodies where a single substitution of an amino acid from the defined epitope causes a loss of antigen recognition, it is expected that there will be little or no significant (e.g., little or no detectable) cross-reactivity between metzincin subfamilies (e.g., ADAMs antibodies should not cross react with MMPs antibodies, and vice versa). However, there may be some cross-reactivity between highly similar subfamily members where amino acid variation in the defined epitope region is conservative. Therefore, in some embodiments, approximately 90% of antibodies raised against the epitopes described herein are expected to be monospecific, with the exception of those metzincins with identical amino acid epitopes (MT1-MMP, MT2-MMP & MT5-MMP). In some embodiments, antibodies can be produced to discriminate between these metzincins by including additional, protease specific, sequences in the immunogenic peptide along with the defined epitope (e.g., N-terminal and/or C-terminal to the defined epitope).

The catalytic domain of metzincins is characterised by the presence of a shared structural scaffold and active site environment, although each subfamily has unique structural elements. Comprising of three alpha helices (αA, αB & αC)

and five beta strands (sI-sV) which form a twisted beta-sheet, the catalytic domain is spatially organised into an N-terminal domain and a C-terminal domain separated by the active site cleft (catalytic cleft) which spans the entire width of the molecule and harbours a catalytically active zinc ion (1,2). A further characteristic structural feature is the presence of an extended C-terminal zinc-binding motif HEXXHXXGXXH (SEQ ID NO: 1) or HEXXHXXGXXD (SEQ ID NO: 2) where X denotes any amino acid and which contains three zinc-binding histidines (or in some metzincins the third histidine is replaced by aspartate) and a glutamate that acts as a general base/acid during catalysis. Note that SEQ ID NO: 1 (with an H at its C-terminus) is characteristic of human and mammalian metzincins whereas SEQ ID NO: 2 (with a D at its C-terminus) is characteristic of certain unicellular organisms. The first two zinc-coordinating histidines of this consensus structural motif exist within the C-terminal half of the active site alpha helix denoted alpha helix B (αB, refs. 1 and 2, and FIG. 1). In FIG. 1, the distinct regions of the catalytic cleft and C-terminus are illustrated to show where inhibitors are believed to make contact. The catalytic cleft antibodies of the present invention bind to a distinct region from those of the hydroxamate inhibitors and the newer generation chemical inhibitor of MMP13. A three dimensional molecular model of the full catalytic domain can be found in refs. 33, and 34. In FIG. 1, a region of the catalytic cleft is indicated by a line that spans from the C-terminal end of alpha helix B through amino acid Z. Amino acid Z represents the sub-family selective residue which forms an important part of the antibody epitope. Amino acid M is the conserved methionine of the Met-turn. A hallmark glycine residue at the end of αB bends the polypeptide chain sharply out of the alpha helix into a descending chain which contains the third zinc-chelating histidine or aspartate. The hallmark glycine (G) is invariably flanked by bulky hydrophobic residues which are also found next to the glutamate base. These non-polar residues are thought to play a structural role in the positioning of αB within the catalytic cleft. Another conserved structure further downstream of αB is that the polypeptide chain characteristically forms a 1,4 β-turn with a methionine strictly conserved at position 3 (Met-turn) which is spatially close to the catalytic zinc yet does not make contact (refs. 1 and 2, and FIG. 1). The Met turn is then followed by a variable region and a C-terminal helix (αC) which completes the catalytic domain. In the reprolysins (includes ADAMs) and matrixins (MMPs) subfamily, the consensus zinc-binding motif invariably contains a third zinc coordinating histidine, e.g., HEXXHXXGXX<u>H</u> (SEQ ID NO: 1). Furthermore, the third histidine is immediately followed by a residue which is mostly conserved between the members of each metzincin subfamily. In some embodiments, the identity of this residue (the residue immediately after the third Histidine, or immediately after the Aspartate for proteases having an Aspartate instead of the third Histidine) is subfamily specific. Accordingly, peptides containing this subfamily specific residue can be used to generate binding agents (e.g., antibodies or antigen-binding fragments thereof) that are specific for particular proteases of a subfamily (or for one or more of a group of proteases that belong to a particular subfamily characterized by the presence of a particular type of amino acid at this position). This residue is an aspartate in the reprolysins, a serine/threonine/valine in the matrixins, a glutamate in the astacins, a valine in the pappalysins and a proline in the serralysins (1-4). Thus, a more specific metzincin catalytic consensus motif may be represented by the sequence HEBXHXBGBXHZ (SEQ ID NO: 3) or HEBXHXBGBXDZ (SEQ ID NO: 4) where X denotes any amino acid, B denotes a variable bulky hydrophobic or non-polar residue (e.g. I, L, F, M, Y, V etc.) and Z denotes the subfamily specific residue referred to herein. Remarkably, in some embodiments, an antibody raised against a peptide immunogen encompassing this metzincin consensus region (SEQ ID NO: 3 or 4) binds specifically to an epitope encompassed within the C-terminal region HXBGBXHZ (SEQ ID NO: 5) or HXBGBXDZ (SEQ ID NO: 6) of the motif. This region contains three highly conserved amino acid positions, the second zinc-coordinating histidine, the hallmark G and the third zinc-coordinating residue most commonly a histidine but also an aspartate (H/D) in a few cases. It also contains the bulky/non-polar residues flanking the hallmark G and the subfamily specific residue (Z), that when coupled to the highly variable residues (X) generate sufficient sequence variation between the metzincins to impart antigenic selectivity. This region is distinct from the region recently termed a "specificity loop" in studies which identified a small molecule inhibitor with selectivity for MMP13 since the "specificity loop" is located after the Met-turn rather than before it in the linear polypeptide sequence (5). Spatially, the binding pocket for this MMP13 inhibitor is deep within the catalytic domain and is away from the catalytic zinc and substrate binding pocket where the peptide immunogen herein described was identified for its immunogenicity (see FIG. 1). Therefore, in some embodiments, antibodies that bind to this region which lies between αB and the Met-turn are protease selective (e.g., they selectively bind to and/or inactivate a single protease or a restricted number of proteases of the metzincin family that have either a unique or similar epitope in this region). Accordingly, some antibodies may be mono-specific whereas others may cross-react with a restricted number of proteases that have a highly similar epitope in this region.

Accordingly, an aspect of the present invention relates to the production of antibodies that inhibit the catalytic activity of metzincins by targeting the catalytic cleft using immunogenic peptides encompassing the metzincin consensus catalytic motif (SEQ ID NO: 3 or 4), yet retain sufficient specificity to distinguish between closely-related members of the same gene subfamily. This is despite the fact that a significant number of residues essential for catalysis and the coordination of the zinc ion are conserved within this region which adopts a shared structural unit comprising the C-terminal portion of αB and the following descending chain which has a crucial role in the coordination of the catalytic zinc ion and which precedes the Met-turn (see Table 2 below). Accordingly, aspects of the invention can be useful to specifically inactivate different members of the metzincin protease family (e.g., specific binding agents such as antibodies can be used to inhibit one or a few related proteases without inhibiting any of the others).

Accordingly, in some embodiments, an antibody is raised against a peptide immunogen consisting of or encompassing the region HXBGBXHZ (SEQ ID NO: 5) or HXBGBXDZ (SEQ ID NO: 6) for one or more specific proteases (see the sequences listed in Table 3). For example an antibody may be raised against a specific peptide having the sequence HXBGBXHZ (SEQ ID NO: 5), or HXBGBXDZ (SEQ ID NO: 6) of a particular metzincin protease of interest or of a particular group of metzincin proteases of interest. In some embodiments, a specific metzincin sequence may be used (e.g., from Table 3). In some embodiments, a plurality (e.g., 2-5, 5-10, or more) of peptides may be used each having a different amino acid sequence corresponding to a different metzincin protease sequence. In some embodiments, the different sequences used may share a particular feature (e.g., the same "Z" amino acid for a particular type of protease as described herein) and have different X and/or B residues corresponding to different metzincin protease sequences of that type of protease. However, it should be appreciated that in some embodiments, an antibody may be raised against a peptide that consists of or includes the conserved amino acids (H, G, H or D, Z of a particular type of protease) of a peptide HXBGBXHZ (SEQ ID NO: 5), or HXBGBXDZ (SEQ ID NO: 6), but for which one or more of the X and/or B residues, or combinations of residues, are substituted for an amino acid or combination of amino acids, that is/are not found in a natural protease sequence.

It should be appreciated that the antibodies may be raised against the HXBGBXHZ (SEQ ID NO: 5), or HXBGBXDZ (SEQ ID NO: 6) peptide itself or against a longer peptide that includes this sequence. The longer peptide may include additional N-terminal and/or C-terminal (e.g., 1-5, 5-10 or more) residues. The additional residues may be those of one or more naturally occurring protease sequences described herein, or sequences that are not found in natural proteases, or a combination thereof. In some embodiments, the peptide may include regions that are C-terminal to alpha helix B (see FIG. 1) and N-terminal to the Met-turn (see FIG. 1). In some embodiments, the peptide includes one or more C-terminal residues of alpha helix B (see FIG. 1), for example about 1-10 C-terminal residues of alpha helix B. In some embodiments, an epitope as described herein may be provided along with a few additional C-terminal amino acids (e.g., 1 or 2). It should be appreciated that the length of the region spanning from the C-terminus of alpha helix B to the Met turn is different in different proteases. Accordingly, in some embodiments, different peptide lengths may be used for raising antibodies against different proteases. However, in some embodiments, peptides of similar (or the same) length may be used for different proteases since the entire length of the peptide spanning this region is not required as described herein.

In some embodiments, a peptide that is used does not include the sequence of an ADAM 15 protease. Accordingly, in some embodiments, an antibody that is generated or used as described herein does not bind to ADAM 15 specifically.

It should be appreciated that the peptides described herein as being useful for raising antibodies (e.g., in a mammal, for example, mouse, rabbit, goat, or other mammal, or in a synthetic screen or other experimental system) also may be used as therapeutic immunogens. For example, one or more peptides described herein may be administered to a subject (e.g., a human patient) to raise antibodies against a particular protease or group of proteases that is over-active in that subject. It should be appreciated that aspects of the invention may be used to produce specific antibodies, assay specific levels or activities, and/or selectively inhibit any one or more proteases of the metzincin family or of a subfamily thereof either in a subject in vivo, or in cells or tissue ex vivo, or in vitro.

It should be appreciated that a binding agent (e.g., antibody) described herein may be used to inhibit one or more metzincin proteases in any subject. A subject may be a human, or other mammal, or other vertebrate, or other organism. In some embodiments, antibodies raised against peptides from one species may cross-react with proteases from other species since the consensus sequence is highly conserved across species (e.g., across mammalian species).

The human genome contains approximately 80 genes belonging to the metzincins and the majority of characterised members are shown in Table 2.

TABLE 2

Metzincins in the Human Genome

| Name | Chromosomal locus |
|---|---|
| ADAM17 | 2p25 |
| ADAM10 | 15q22 |
| ADAM2 | 8p11.2 |
| ADAM7 | 8p21.2* |
| ADAM8 | 10q26.3* |
| ADAM9 | 8p11.23 |
| ADAM11 | 17q21.3* |
| ADAM12 | 10q26.3* |
| ADAM15 | 1q21.3* |
| ADAM18 | 8p11.22 |
| ADAM19 | 5q32-q33* |
| ADAM22 | 7q21* |
| ADAM23 | 2q33* |
| ADAM28 | 8p21.2* |
| ADAM32 | 8p11.23 |
| ADAM33 | 20p13* |
| ADAMDEC1 | 8p21.2* |
| ADAMTS2 | 5qter |
| ADAMTS3 | 4q21.1* |
| ADAMTS14 | 10q2* |
| ADAMTS16 | 5p35 |
| ADAMTS18 | 16q34 |
| ADAMTS7 | 15q24.2 |
| ADAMTS12 | 5q35 |
| ADAMTS9 | 3p14.3-p14.2 |
| ADAMTS20 | 12q12 |
| ADAMTS6 | 5pter-qter* |
| ADAMTS10 | 19p13.1* |
| ADAMTS1 | 21q21.2* |
| ADAMTS4 | 1q21-q23* |
| ADAMTS5 | 21q21.3* |
| ADAMTS8 | 11q25* |
| ADAMTS15 | 11q25* |
| Papilin | 14q24.2 |
| ADAMTSL1 | 9p22.1* |
| ADAMTSL2 | 9q34.2 |
| ADAMTSL3 | 15q25* |
| ADAMTSL4 | 1q21.2 |
| ADAMTSL5 | 19p13.3 |
| BMP-1 | 8p21 |
| Tolloid-like 1 | 4q32-q33 |
| Tolloid-like 2 | 10q23-q24 |
| Meprin 1A | 6p21 |
| Meprin 1B | |
| MMP1 | |
| MMP3 | |
| MMP8 | |
| MMP 10 | |
| MMP 11 | |
| MMP 12 | |
| MMP 13 | |
| MMP 23A & B | |
| MMP27 | |
| MMP19 | 12q14 |
| MMP26 | 11p15 |
| MMP28 | 17q11-q21.1 |
| MMP21 | 10q26.2 |
| MMP17 | 12q24.3 |
| MMP25 | 16p13.3 |
| MMPL1 | 16p13.3 |
| MMP14 | 14q11-q12* |
| MMP15 | 16q13-q21* |
| MMP16 | 8q21* |
| MMP24 | 20q11.2* |
| MMP2 | 16q13-q21* |
| MMP7 | 11q21-q22 |
| MMP9 | 20q11.2-q13.1* |
| MMP20 | 11q22.3 |

*indicates that related genes within the sub-clade are located in paralogous regions of the human genome. Adapted from Huxley-Jones et al. BMC Evolutionary Biology 2007 7:63 doi: 10.1186/1471-2148-7-63 Ref. 18.

Two important subfamilies of the metzincins, the matrixins and the reprolysins, represent the matrix metalloendoproteinase (MMPs) and the disintegrin-metalloendoproteinases (ADAMs/ADAM-TS) gene families respectively (3,4).

Both the MMPs and ADAMs/ADAM-TS families are now known to play important roles in both health and disease. Like other metzincins, ADAMs and MMPs share a modular architecture where the activity of metalloprotease domain is regulated by a prodomain in which a cysteine residue coordinates the metalloprotease catalytic cleft zinc ion. Thus, metzincin proteases are constitutively expressed, but remain in a latent state until activated by enzymes that cleave the pro-domain or free the cysteine bond. These metzincins are also regulated by endogenous inhibitors including TIMPs, RECK and α-macroglobulin, of which the TIMPs are the most important and well-studied.

MMPs, encoded by 24 human (Table 2) and 23 mouse genes, include secreted and membrane associated members divided into four main subgroups according to their domain structure, including collagenases, stromelysins, gelatinases, and membrane-type MMPs (MT-MMPs). The majority are soluble extracellular proteases whose primary role is the degradation and/or remodelling of the extracellular matrix (ECM), although several reports have shown intracellular MMP functions as well as active forms of MMP-2, -9, and -13 in the nuclei of neurons and glial cells (6). Membrane localised members such as MMP14 (MT1-MMP) are single span integral membrane proteins that also shed cell surface proteins and activate latent MMPs. MMPs play crucial roles in many physiological processes such as wound healing, angiogenesis and neuronal development (4, 7). They also have important roles in the progression of numerous pathologies. Taking cancer as a prominent example, MMPs are known to be up regulated in tumours and are often associated with poor prognosis. For example, the expression of MMP-11 and/or MMP-14 is a negative prognostic indicator for small-cell lung cancer. In addition, MMP-1 and MMP-9 expression are associated with poor prognosis for primary human breast carcinoma (6). In glioma, multiple MMPs are up-regulated including MMP-1, -7, -10, -11, and -19 and the well-studied gelatinases, MMP-2 and MMP-9 (6). Several MMPs exert anti-tumour effects, including MMP-3, -8, -9, -11, -12, -19, and -26. (7). For example, expression of MMP12 in colon carcinoma is associated with increased patient survival (7). MMP expression is associated with both cancer cells (e.g., MMP7) and stromal cells (e.g. MMPs 2 & 9), which include fibroblasts, myofibroblasts, inflammatory cells and endothelial cells. MMPs promote cancer by increasing cancer cell growth, invasion, metastasis and angiogenesis through degradation and remodelling of ECM components, the mobilisation of growth factors from the cell surface and the ECM and via signalling (4,7). Angiogenesis is a target for cancer therapy but while MMPs such as MMP2, MMP 9 & MMP14 are necessary for promoting angiogenesis, endogenous angiostatic agents such as Angiostatin, a product of plasminogen, is produced by enzymatic action of MMP2, MMP3, MMP7, MMP9 and MMP12 in vitro. Another endogenous angiogenesis blocker, Endostatin, is generated from type XVIII collagen by MMP3, MMP9, MMP12, MMP13 and MMP20 processing in vitro (7). These examples highlight the importance of target validation for therapeutic inhibition of MMPs and offer insight into why broad spectrum inhibitors targeting tumour progression have failed as a consequence of the inhibition of desirable MMP activities in addition to the projected undesirable activities. Furthermore, the increased expression of TIMPs (tissue inhibitor of metalloendoproteinase) gene family members is generally associated with poor prognosis indicating varying roles for different MMP family members (3, 7).

In contrast with MMPs, ADAMs disintegrin-metalloproteases are predominantly integral membrane proteins although some soluble isoforms (e.g., sADAM12) are generated by alternate splicing of their mRNA (4, 9). A distinct branch of the ADAM referred to ADAM-TS are exclusively soluble, secreted molecules which distinctly contain one or more C-terminal thrombospondin repeats and the absence of a membrane spanning helix and cytoplasmic domain (4). Like MMPs, the ADAMs gene family play an important role in cancer progression. Though only approximately 60% of ADAMs family members are proteolytically active as predicted by the presence of the conserved metzincin zinc-binding motif, research has established ADAMs proteins as important cellular sheddases, regulating through targeted proteolysis cellular processes including mobilisations of cytokines, growth factor signalling and cell-cell adhesion. Important ADAMs cellular targets include pro-inflammatory cytokines such as TNFα, growth factor ligand—receptor systems such as the ErbB receptors and their ligands (4, 9-14), Notch receptors for activation and adhesion molecules such as members of the cadherin family (4). Elevated expression of several catalytically active ADAMs family members have been reported for distinct tumours. For example, ADAM 17, the TNFα converting enzyme (TACE) is elevated in carcinomas of the brain, breast, colon, stomach, kidney, liver, lung, ovary, pancreas and prostate, whereas ADAM 19 elevation is restricted to tumours of the brain and kidney (4). ADAM 17 expression in breast cancer has been correlated with variables of tumour progression (4). INCB3619, a partially selective, small molecule proteolytic inhibitor of ADAM 10 and ADAM 17, has been shown to synergize with paclitaxel in retarding the growth of breast cancer tumours (14). INCB3619 has also been shown to act synergistically with paclitaxel to reduce tumour volume in a mouse model of non-small-cell lung cancer (10). Furthermore, ADAM 12 levels in the urine of patients have been correlated with breast cancer progression, suggesting that ADAM 12 may be a diagnostic marker for breast cancers (11). ADAM 12 has been reported to be predominantly expressed in glioblastomas where it mobilises proHB-EGF and was inhibited by treatment the hydroxamate inhibitor KB-R7785 (11, 12). ADAM 15, originally identified in vascular cells, is up regulated in breast, lung, gastric and prostate cancers and the chromosomal region containing its gene (1q21.3) is amplified in several cases (4, 15, 16). With regard to prostate cancer, ADAM 15 is thought to play a role in disease progression as elevated ADAM 15 expression in diseased tissue correlated with metastasis and high-grade disease/poor prognosis as assessed by the Gleason score (15). Furthermore, a splice variant of ADAM 15 containing an inserted binding site for Src within the cytoplasmic domain (ADAM 15-B) was linked to poor survival in node negative breast cancer (16). This variant was shown to possess 2-3-fold higher catalytic activity compared to non-Src binding ADAM 15 variants in a cell-based shedding assay (17). These studies are the first to link ADAMs catalytic activity with tumour aggressiveness.

The ADAM-TS subfamily of reprolysins is also emerging as important in health and disease. Of the nineteen human proteins, arguably the best characterised member is ADAM-TS-13, the von Willebrand Factor (vWF) cleaving enzyme, which antagonises vWF multimerisation during haemostasis. Patients with thrombotic thrombocytopenic purpura characterised by the presence of ultra large vWF multimers in their serum develop autoantibodies that inhibit ADAM-TS-13-mediated cleavage of vWF (17). Significantly, the epitopes for these autoantibodies have been mapped to regions outside of the catalytic domain (19). ADAM-TS members collectively termed aggrecanases (ADAM-TS-1, -4, -5, -8, -9, 15 & -20) play a major role in arthritis progression through proteolytic breakdown of the cartilage component hyalectan (20). ADAM TS-7 and -12, elevated expression also correlate with disease progression and have been shown to breakdown cartilage oligomeric matrix protein (COMP) (20). Interestingly, a recent genetic study has identified ADAMTS-7 as promoter of atherosclerosis (21).

In addition to the MMPs and ADAMs/ADAM-TS mentioned above, the astacins and pappalysins are also associated with disease. Astacins, such as the meprins and BMP-TLL (bone morphogenetic protein and toloid-like metalloproteinases) are also becoming increasingly relevant to the progression of several pathologies (22-24). For example, the meprins promote inflammatory processes linked to acute renal failure (ARF), urinary tract infections (UTI) and inflammatory bowel disease (23). A non-specific inhibitor of meprins, actinonin, was shown to attenuate the extent of renal damage in rodent models of ARF (22). Furthermore, a study of meprin expression in human urine identified a correlation between high meprin A protein levels and active UTI (23). Taken together, the data implicate a role for meprins in renal and urogenital pathologies. BMP-TLL's are known to be involved in biogenesis of the ECM and its modulation during morphogenetic processes including the processing of pro-collagens I-III for collagen fibril formation and the TGF-beta-like "chalones" growth differentiation factor 8 (GDF8, also known as myostatin), and GDF11 (also known as BMP11), involved in negative feedback inhibition of muscle and neural tissue growth, respectively (24). The pappalysins, which include pappalysin A, known to cleave IGF-binding proteins, has been shown to correlate with pre-eclampsia progression (25).

Accordingly, aspects of the invention provide agents for detecting and/or targeting different members of the MMP and ADAM gene families, or of other metzincin subfamilies as described herein that are desirable targets for therapeutic intervention in diseases or disorders (e.g., cancer and/or several additional pathologies). Agents of the invention provide significant advantages over existing protease inhibitors. Currently, the lack of specific inhibitors for metzincins in general and for members of MMP and ADAMs gene families, in particular, has proven to be a major obstacle in the evaluation and/or treatment of diseases and conditions associated with different metzincin protease activity. The naturally occurring inhibitors, TIMPs, of which four are found in humans, are in general terms, broad-spectrum inhibitors of the 23 MMPs found in humans, although some differences in specificity exist among them. TIMP-1 is more restricted in its inhibitory range than the other three TIMPs, having a relatively low affinity for the membrane-type MMPs, MMP-14, MMP-16, and MMP-24 as well as for MMP-19 [4]. TIMP-3 is unique among the mammalian TIMPs in inhibiting a broader array of metzincins including several members of the ADAM and ADAMTS families (4). Furthermore, studies with naturally occurring TIMPs suggested that these inhibitors may have cancer promoting properties independent of their MMP and ADAM blocking function and this led to a focus upon the development of synthetic active site inhibitors (27). Initially, synthetic inhibitors focused upon chemical groups that chelated the zinc ion within the active site (e.g. hydroxamate). A major problem with inhibitors based around this concept is the issue of selectivity. For example with the MMP's, selectivity is determined in the peptidomimetic backbone but it does not confer total selectivity and other non-related metal chelating enzymes and other members of the metzincins spanning subfamilies are usually inhibited (5,6, 27). This lack of selectivity was a major reason for the failure of the early generation of MMP inhibitors when used clinically. However, subsequent clinical trials of MMP inhibitors for the treatment of cancer, cardiovascular disease and anti-angiogenesis have also largely failed (3,8). In general, target validation has been generally poor and inhibitors have lacked sufficient specificity to select and target pathologic members of the matrixins and in some cases other subfamilies of the metzincins such as the ADAMs. Consequently, the approach of using chemical inhibitors, particularly derivatives of hydroxamate and butanoic acid, is considered to have inhibited both desirable activities of MMPs as well as undesirable activities, leading to non-achievement of the clinical endpoint or even increased disease progression. For example, the MMP inhibitor marimastat failure can partially be ascribed to its general broad inhibitory profile including many members of the metzincin family such as ADAM's 9, 10, 17, and 33 (4, 8). With respect to purported selective ADAMs inhibitors, the most impressive compound to date has been INCB7839 developed by Incyte Corporation. This compound is related to its predecessor INCB3619 and although both utilize a hydroxamate as the zinc-binding group, do show some selectivity towards ADAMs 10 and 17 over other family members such as ADAMs 8, 9 and 33 (10). However, it should be noted that INCB3619 inhibited MMP's 2, 12 and 15 at a similar dose rage as that for its effect on ADAMs 10 and 17 indicating that like earlier generation hydroxamate derivatives, its selectivity was not restricted between metzincin subfamilies or their individual members (10).

The growing realization that members of metzincins and in particular the MMP's have both desirable and undesirable roles in pathology is now an important factor with respect to designing inhibitors which display a much greater selectivity towards individual family members regarded as disease-promoting and thus clinical targets (8). With respect to this aim, there has been a shift in focus away from compounds whose inhibitory efficacy is dependent on interacting with the catalytic $Zn^{2+}$ ion (5,6,8). For example, screening of a chemical library identified a selective, non-metal binding, MMP13 inhibitor which binds in the S1' specificity loop located between the Met-turn and αC and away from the substrate binding cleft. This non-metal binding compound is structurally distinct from zinc-binding hydroxamate and is thought to inhibit catalysis non-competitively by restricting the flexibility of the S1' "specificity" loop (5). Similarly, with regard to the ADAMs, structure function studies have implied that substrate recognition within the membrane environment requires molecular contact over multiple domains including the disintegrin and cysteine rich domains which are proximal to the catalytic domain. Therefore, there is significant interest in targeting these regions as a means to acquiring the desired specificity for inhibitors of catalytic activity (4,6,8).

In addition to therapeutic compounds, measurement of the catalytic activity of specific MMPs and ADAMs is also desirable for diagnostic and prognostic applications. The known roles for various MMPs and ADAMs in the processes associated with the progression of cancer including tumour growth, metastasis, and angiogenesis, identify specific MMPs and ADAMs molecules as important biomarkers of disease progression (3,4,6,8). However, methods for the measurement of MMP activity in complex biological samples is complicated by the absence of specific physiological or synthetic substrates for family members and the duration and complexity of assays incorporating protein substrates. For example, zymography is the preferred method for the measurement of gelatinase activity and involves incorporating the gelatin substrate into denaturing polyacrylamide gels used to separate complex mixtures of proteins. Following renaturation of the separated protein sample, visualisation of gelatinase activity is accomplished by staining of the gels showing up clear zones of lysis at apparent molecular weights corresponding to the MMP under investigation. Such assays, while sensitive and quantitative, may take more than 24 hours to perform and are not suitable for MMPs lacking specificity toward gelatin e.g., MMPs 1, 7 and 13 (27). More rapid assays exploit the use of peptide substrates designed to incorporate fluorescent groups juxtaposed to a quenching group within a specific peptide derived from a larger protein substrate. The cleavage of the peptide bond separates the two groups allowing for an increase in fluorescence detection (fluorescence energy transfer quenching). This is necessary as metalloendoproteinases recognise amino acids on both flanks of the peptide cleavage bond unlike serine proteases where the amino acid C-terminal to the peptide cleavage bond can be replaced by a fluorescent group (28-29). These labelled peptide substrates offer good sensitivity and vastly superior assay completion times but specificity is introduced by immunocapture of the MMP to be detected from the biological sample using specific antibodies immobilised upon a surface (29). These antibodies are known to bind selectively to particular proteases, but not to inactivate them. Accordingly, current assays are based on techniques designed to capture most or all of one or more specific proteases in a sample and then to evaluate their activity using peptide substrates (e.g., labelled substrates) that are not protease specific in that they can act as substrates for a broad range of proteases. In some embodiments, such assays depend upon the complete capture of the target MMP from a biological sample by the specific antibody in order to quantify MMP activity. In contrast, the presently described selective inhibitory antibodies can be used to evaluate the activity of one or more predetermined metzincins in a biological sample without needing to separate out the different proteases prior to performing an assay. In some embodiments, the protease activity in a sample can be assayed using a non-specific substrate in the presence and in the absence or one or more selective antibody inhibitors described herein. The measured level of activity in the presence and absence of the selective antibodies can be compared, subtracted, or otherwise evaluated to determine the contribution (e.g., relative contribution) of each predetermined protease to the total protease activity in a sample. This can be used to determine the level of activity of each predetermined protease of interest in a biological sample.

With regard to ADAMs proteins, certain methods to assess catalytic activity have benefited from the industry's experience of MMPs. Fluorescently quenched peptide substrates designed for MMPs have been observed to be hydrolysed by ADAMs members albeit with reduced efficiency (30,31). The first fluorescent peptide substrate developed for measurement of ADAMs catalytic activity utilised the TNFα cleavage peptide recognised by ADAM 17 (30). Using this as a template, Moss and Rasmussen developed derivatives that were efficiently cleaved by ADAMs 17, 8, 10 and 12 and useful for high-throughput screening studies (30). Furthermore, Fourie et al. (32) identified that ADAM 15, 8 and MDC-L (ADAM 28) had a similar substrate specificity profile after a screen of a peptide library and were all able to cleave CD23 from the cell surface, thereby providing further templates for fluorescent substrate design. These studies confirm that peptides substrates for the assessment of the catalytic activity of ADAMs and MMPs are available but as these substrates are hydrolysed by several family members, the specificity needed for measurement of individual target metzincin activity within a biological sample remains elusive. It should be noted that the assays described above are used for metzincins that function in a soluble environment, that is, do not require a native cellular membrane for their efficient catalytic function. Assays for ADAMs and MT-MMPs described above require isolated catalytic domains prepared recombinantly or the entire extracellular portion of the molecule devoid of its membrane anchoring alpha helix and intracellular regions. Determining the catalytic activity of ADAMs and MT-MMPs in tissue samples requires the preparation of cell suspensions or monolayers from the tissue by established procedures such as mechanical or enzymatic tissue disruption and separation of a cellular material Amidst this background in the art, aspects of the present invention provide methods and compositions that are useful to define an assay format for the measurement of the catalytic activity of a target metzincin such as an MMP or ADAM within a complex biological sample including tissue biopsies and bodily fluids (e.g., samples from diseased tissue such as biopsies of pre-cancerous and cancerous tissues, biopsies of inflammatory tissues such as the gut or joints, and/or any suitable biological sample, including, but not limited to: blood, serum, urine, stool, sputum, synovial fluid, cerebrospinal fluid, pleural fluid, peritoneal fluid, peritoneal lavage fluid, peritoneal dialysate, pericardial fluid, and general serous fluids, etc., or any combination thereof).

In some embodiments, a unique aspect of the invention is the production and/or application of antibodies with exquisite specificity against predetermined proteases described herein. For example, certain ADAM15 antibodies have an IC50 of approximately 60 nM in cell-based assays. This indicates that the antibodies are high affinity, with binding constants in the high picomolar to mid nanomolar range. These antibodies also recognize an approximately 6-7 residue, structural epitope within the consensus metzincin catalytic motif of which 4 amino acids are variable residues. This binding specificity causes these antibodies to specifically neutralize the catalytic activity of the target metzincin family member within a sample. Similarly, specific inhibitory antibodies against other metzincin proteases (e.g., each with a picomolar to nanomolar binding constant for a particular target protease, and/or an inhibitory $IC_{50}$ of about 20-200 nM, for example about 60 nM in a cell-based assay) can be produced using a peptide immunogen incorporating the corresponding catalytic cleft epitope (Table 3). Therefore, an accurate estimation of the target metalloendoproteinase activity within the sample can be made even by use of broad specificity fluorescent peptide substrates or equivalents by following and/or comparing the activity of the target metalloendoproteinase within a biological sample in the absence and presence of the specific catalytic-cleft directed antibody. The reduction in activity of the antibody-treated sample as compared to an identical sample that has not been treated with a specific catalytic cleft-directed antibody corresponds to the activity attributed to the metzincin (or group of metzincins) that is/are specifically inactivated by the antibody. It should be appreciated that in some embodiments, two or more different antibodies that specifically inactivate a particular metzincin(s) may be used to assay a sample for the activity of that metzincin(s) (e.g., to determine an absolute level of activity or a relative level of activity, for example, a percentage contribution to activity) in the sample. However, it also should be appreciated that in some embodiments, two or more different antibodies may be used to evaluate the activity (e.g., to determine an absolute level of activity or a relative level of activity, for example, a percentage contribution to activity) of two or more metzincins in a sample.

In order to study the biological role of ADAM 15, polyclonal antibodies directed to a catalytic cleft derived peptide encompassing amino acids 346-359 ($^{346}$IAHEL-GHSLGLDHD$^{359}$) (SEQ ID NO: 7) were generated, ascribing position 1 to the initiating methionine of ADAM 15, see Table 3 (and refs. 33, and 34). According to aspects of the present invention, this region corresponds to the C-terminal portion of the catalytic/active site alpha-helix (αB, and refs. 1 and 2) and the descending chain characterised by the presence of the hallmark G residue that permits a sharp turn of the polypeptide chain. The region encompasses the consensus metzincin catalytic motif HEBXHXBGBXHZ (SEQ ID NO: 3) where the third zinc coordinating histidine is followed by a subfamily-specific aspartate in the catalytically active ADAMs. Two distinct antibodies showed exquisite specificity for ADAM 15, not cross-reacting with equivalent peptides derived from the corresponding regions of several other ADAMs or MMPs (33,34). Epitope analysis revealed that both antibodies recognised a region within the C-terminal portion of the peptide including $^{352}$HSLGLDHD$^{359}$ (SEQ ID NO: 8) and that the subfamily specific residue D$^{359}$ was an important residue of both epitopes. This likely explains why these ADAM 15 antibodies do not cross-react with MMPs which have a S/TN in this position. These antibodies, therefore, displayed not only the ability to discriminate between individual subfamily members of the metzincins, e.g., between individual ADAMs, but also between closely related subfamilies, e.g., between ADAMs and MMPs, a feature not observed for either early or late generation chemical inhibitors that target the catalytic zinc. These antibodies also selectively inhibit ADAM 15 shedding activity in a cell-based assay widely used to assess ADAM catalytic activity and do not inhibit the activity of other ADAMs that shed the same substrate. The use of antibodies to target the catalytic cleft consensus region of metzincins and neutralise their catalytic activity represents a novel approach to the generation of highly selective metzincin inhibitors. It is remarkable that the peptide immunogens described herein are highly antigenic and can confer antigenic selectivity as these regions are conserved between species and could be viewed as poorly immunogenic. It is also remarkable that molecules as large as immunoglobulins are able to bind with high affinity to this catalytic cleft region between αB and the Met-turn (FIG. 1). Antibodies to surface loop regions of MMP14 (MT1-MMP) that block catalytic function have been reported previously but were not directed towards the catalytic cleft (36) and as mentioned above autoantibodies that inhibit the activity of ADAM-TS-13 do not bind within the metalloprotease domain of the molecule. Therefore, certain embodiments of the present invention provide an assay for the measurement of ADAM 15 catalytic activity in tissue samples derived from prostate or breast cancer patients without being bound to either this particular metzincin or by a particular pathology/disease sample.

According to aspects of the invention, specific antibodies to other metzincin family members can be developed using specific catalytic cleft epitopes. For example, Table 3 shows catalytic cleft peptides that can be used to generate specific antibodies that bind to specific members of the consensus metzincin catalytic motif of SEQ ID: NO 3. The corresponding regions of different metzincins, including ADAMs and MMP family members, are shown for comparison. The third zinc coordinating histidine in each of these examples is followed by a subfamily-specific residue. Each of these regions (or a smaller fragment thereof containing a specific epitope, or a larger fragment containing these regions or an epitope thereof but not C-terminal to the Met-turn, and/or not including the Met of the Met-turn) can be used to produce selective antibodies that are useful to assay and/or inhibit therapeutically (e.g., in a subject) one or more particular metzincin proteases as described herein.

In some embodiments, in order to produce a metzincin antibody that cross-reacts with different subsets of metzincin proteases, a minimal epitope from catalytic cleft that shares sequences between different proteases could be used and some generic peptide (non-protease specific sequences) could be added at the N-terminal and/or C-terminal side(s) to provide structure (for example, a helical structure at the N-terminal side). In contrast, to generate a monospecific antibody, specific epitope peptides (optionally with protease specific N-terminal and/or C-terminal peptides) could be used to raise the antibodies.

Similarly, the equivalent regions of other metzincins found in humans that are desirable therapeutic targets can be used to generate highly selective inhibitory antibodies. Examples include but are not limited to those sequences shown in Table 3.

In some embodiments, one or more antibodies described herein are provide for therapeutic applications. One of skill in the art can determine appropriate doses and/or therapeutic regimens for different antibodies of interest. For example, appropriate levels and timings of administration can be determined to achieve desired therapeutic outcomes. In some embodiments, a treatment described herein may result in a cure (for example a complete remission of or end to a disease or condition being treated). However, in some embodiments, a therapeutic treatment may be useful if it slows, reduces (e.g., partially), or prevents the progression of a disease or condition being treated.

In some embodiments, one or more antibodies and or peptides (e.g., epitopes and/or immunogens) may be provided for therapeutic use (e.g., in a pharmaceutically orvphysiologically compatible buffer along with one or more additional stabilizers or excipients or other therapeutic agents, and sterilized for example). In some embodiments, the mode of administration is parenteral, e.g. intraperitoneal, intravenous, subcutaneous, intramuscular, intracavity or transdermal, although any other appropriate mode may be used, for example oral administration. In certain embodiments, intravenous injection or infusion may be used. Any appropriate site of administration may be used. For example they may be administered locally and directly at the site where action is required or may be attached or otherwise associated, e.g., conjugated, with entities which will facilitate the targeting to an appropriate location in the body.

In certain embodiments, any physiologically compatible carrier, excipient, diluent, buffer or stabilizer can be used in the compositions of the invention. Examples of suitable carriers, excipients, diluents, buffers and stabilizers include one or more of water, saline, phosphate buffered saline, dextrose, glycerol, ethanol and the like, as well as combinations thereof. In some cases isotonic agents, e.g., sugars, polyalcohols (e.g., mannitol, sorbitol), or sodium chloride may be included. Compositions may additionally include lubricating agents, wetting agents, emulsifying agents, suspending agents, preserving agents, sweetening agents, flavouring agents, and the like. In certain embodiments, compositions of the invention may be formulated so as to provide quick, sustained or delayed release of the active ingredient after administration to the subject by employing procedures well known in the art. As described herein, in certain embodiments, a composition is in a form suitable for injection and suitable carriers may be present at any appropriate concentration, but exemplary concentrations are from 1% to 20% or from 5% to 10%. Therapeutic compositions typically must be sterile and stable under conditions of manufacture and storage. Appropriate ways of achieving such sterility and stability are well known and described in the art.

In certain embodiments, in addition to an antibody, antigen-binding fragment thereof, and/or peptide described herein, the composition may further comprise one or more other active ingredients such as other agents which are useful for treating cancers, in particular breast, prostate cancer, glioma, non-lung cell carcinoma or colorectal cancer. However, other cancers may be treated as aspects of the invention are not limited in this respect. Suitable additional active agents for inclusion in a composition that is to be used in the treatment of mammals will be known to a person skilled in the art and can be selected depending on the nature of the disease which is to be treated by the composition. Suitable additional agents include antibodies which bind to other targets, cytokines, and chemical agents, e.g., standard chemotherapeutics (small molecule drugs), radiotherapy or drugs controlling side effects For breast cancer treatment suitable additional agents might include anti-Her2/EGFR targeting agents (e.g., Herceptin or Tykerb), anti-neoplastic agents (e.g., Doxil or taxotere) or Avastin. In some embodiments, combined anti-angiogenic formulations are provided, e.g., combining an antibody or antigen-binding fragment of the invention with an anti-angiogenic agent, e.g., a angiopoietin, angiostatin and/or endostatin. In some embodiments, for prostate cancer treatment suitable additional agents might include anti-androgen therapeutic agents (e.g., Zytiga), anti-neoplastic agents (e.g., Taxotere or Jevtana) or Avastin. In some embodiments, combined anti-angiogenic formulations are provided, e.g., combining an antibody or antigen-binding fragment of the invention with an anti-angiogenic agent, e.g., a angiopoietin, angiostatin and/or endostatin. In some embodiments, for glioma treatment suitable additional agents might include anti neoplastic agents (e.g., Temozolomide) or Avastin. In some embodiments, combined anti-angiogenic formulations are provided, e.g., combining an antibody or antigen-binding fragment of the invention with an anti-antiangiogenic agent, e.g., a angiopoietin, angiostatin and/or endostatin. In some embodiments, for non-lung cell carcinoma, suitable additional agents might include anti neoplastic agents (e.g., Cisplatin) or Avastin. In some embodiments, combined anti-angiogenic formulations are provided, e.g., combining an antibody or antigen-binding fragment of the invention with an anti-angiogenic agent, e.g., a angiopoietin, angiostatin and/or endostatin. In some embodiments, for colorectal cancer suitable additional agents might include anti-EGFR inhibitors (e.g., Cetuximab), anti-neoplastic agents (e.g., Oxaliplatin or Irinotecan) or Avastin. In some embodiments, combined anti-angiogenic formulations are provided, e.g. combining an antibody or antigen-binding fragment of the invention with an anti-angiogenic agent, e.g., a angiopoietin, angiostatin and/or endostatin.

Suitable doses of an antibody or antigen-binding fragment thereof, and/or peptide of the invention, alone or with any other active ingredients (if included) will vary from patient to patient and will also depend on the nature of the particular disease. In some embodiments, said dosages constitute a therapeutically effective amount or a prophylactically effective amount, depending on the nature of the treatment involved. Suitable doses can be determined by the person skilled in the art or the physician in accordance with the weight, age and sex of the patient and the severity of the disease. The ability of the binding protein to elicit a desired response in the individual will also be a factor. Exemplary daily doses are: 0.1 to 250 mg/kg, or 0.1 to 200 or 100 mg/kg, or 1 to 50 or 1 to 10 mg/kg, of the active ingredient. This can be administered as a single unit dose or as multiple unit doses administered more than once a day. It is to be noted however that appropriate dosages may vary depending on the patient and that for any particular subject, specific dosage regimes should be adjusted over time according to the individual needs of the patient. Thus, the dosage ranges set forth herein are to be regarded as exemplary and are not intended to limit the scope or practice of the claimed composition.

In some embodiments, a peptide (e.g., epitope and/or immunogenic peptide as described herein) may be used as a vaccine to elicit an immune response in a subject. Typically, a vaccine dose is about 1-5 mgs of peptide. However, other amounts may be used and similar considerations to those described above may be used. In some embodiments, an immunogenic peptide (e.g., as a vaccine) may be administered to a subject in addition to an antibody as described herein (e.g., administered at the same time or in overlapping dosing regimens).

It should be appreciated that aspects of the invention may be used to raise any suitable antibody composition, including, but not limited to whole antibodies (IgG, IgE, IgA, IgM or IgD), polyclonal antibodies, monoclonal antibodies, humanised antibodies, chimeric antibodies, human antibodies and totally synthetic and/or recombinant antibodies generated in bacteria, yeast and/or other recombinant expression systems which may be engineered to contain Fab regions with selectivity for distinct metzincins.

One skilled in the art can produce suitable antibodies based on the epitopes/immunogens described herein using any suitable technique including, but not limited to, immunizing animals and obtaining polyclonal antibodies, or isolating and generating monoclonal antibody producing cell lines (e.g., hybridomas), and/or engineering recombinant antibody producing cells, therapeutic humanization, etc., or any combination thereof. Immunisation can incorporate carrier antigens chemically coupled to the metzincin peptide immunogen (e.g., Keyhole Limpet Haemocyanin KLH) and various adjuvant excipients known in the art.

TABLE 3

| Metzincin | Catalytic cleft peptide immunogen | |
|---|---|---|
| ADAM 15 | IAHELGHSLGLDHD* | (SEQ ID NO: 7) |
| ADAM 8 | MAHEMGHNLGMDHD | (SEQ ID NO: 9) |
| ADAM 12 | LAHELG HNFGMNHD | (SEQ ID NO: 10) |
| ADAM 17 | TTHELGHNFGAEHD | (SEQ ID NO: 11) |
| ADAM 10 | FAHEVGHNFGSPHD | (SEQ ID NO: 12) |
| ADAM 7 | MAHQLGHNLGMQHD | (SEQ ID NO: 13) |
| ADAM 9 | VAHELGHNLGMNHD | (SEQ ID NO: 14) |

TABLE 3-continued

| Metzincin | Catalytic cleft peptide immunogen | |
|---|---|---|
| ADAM 19 | MAHEMGHNFGMTHD | (SEQ ID NO: 15) |
| ADAM 28 | MAHEMGHNFGMFHD | (SEQ ID NO: 16) |
| ADAM 33 | MAHEIGHSLGLSHD | (SEQ ID NO: 17) |
| ADAM TS-2 | VAHETGHVLGMEHD | (SEQ ID NO: 18) |
| ADAM TS-4 | AAHELGHVFNMLHD | (SEQ ID NO: 19) |
| ADAM TS-5 | VAHEIGHLLGLSHD | (SEQ ID NO: 20) |
| ADAM TS-7 | VAHELGHSFGIQHD | (SEQ ID NO: 21) |
| ADAM TS-14 | IAHETGHVLGMEHD | (SEQ ID NO: 22) |
| MMP1 | AAHELGHSLGLSHS | (SEQ ID NO: 23) |
| MMP 9 | AAHEFGHALGIDHS | (SEQ ID NO: 24) |
| MMP 3 | AAHEIGHSLGLFHS | (SEQ ID NO: 25) |
| MMP 2 | AAHEFGHAMGIEHS | (SEQ ID NO: 26) |
| MMP7 | ATHELGHSLGMGHS | (SEQ ID NO: 27) |
| MMP10 | AAHELGHSLGLFHS | (SEQ ID NO: 28) |
| MMP11 | AAHEFGHVLGLQHT | (SEQ ID NO: 29) |
| MMP12 | AVHEIGHSLGLGHS | (SEQ ID NO: 30) |
| MMP13 | AAHEFGHSLGLDHS | (SEQ ID NO: 31) |
| MMP19 | AAHEVGHALGLGHS | (SEQ ID NO: 32) |
| MT1-MMP | AVHELGHALGLEHS | (SEQ ID NO: 33) |
| MT2-MMP | AVHELGHALGLEHS | (SEQ ID NO: 34) |
| MT5-MMP | AVHELGHALGLEHS | (SEQ ID NO: 35) |
| MT-6MMP | AVHEFGHALGLGHS | (SEQ ID NO: 36) |
| Meprin Aβ | VQHEFLHALGF WHE | (SEQ ID NO: 37) |
| Meprin Aα | IEHEILHA LGFYHE | (SEQ ID NO: 38) |
| BMP 1 | VVHELGHVVG FWHE | (SEQ ID NO: 39) |
| TLL 1 | VVH ELGHVIGFWH E | (SEQ ID NO: 40) |
| Consensus | XXHEBXHXBGBXHZ | (SEQ ID NO: 41) |

*SEQ ID NO: 7 Peptide immunogen used to generate ADAM 15 antibodies.
X denotes any amino acid. B denotes a bulky, non-polar amino acid & Z denotes either D, S/T, E,V or P.
Note:
MT1-MMP, MT2-MMP & MT5-MMP share identical motifs.

EXAMPLES

In some non-limiting embodiments, an assay includes or consists of one or more of the following components:

1. A treated biological sample containing the target metzincin(s) for measurement: The sample will be developed appropriately for the metzincin in question as soluble family members are catalytically active in solution whereas membrane associated metzincins such as ADAMs require maintenance of the native cell membrane. Therefore, for soluble metzincins, the sample may be derived from a bodily fluid or processed from a tissue to generate a soluble fraction. The sample may be treated with appropriate excipients to produce an appropriate soluble assay sample optimised for catalysis of a particular metzincin. Without being bound by any particular formulation, excipients may include detergent-based lysis solutions, appropriate polar and non-polar solvents, metal ions and a buffering agent(s) to maintain optimal pH. For metzincins requiring native cell membranes, tissue samples will be treated using established methods to obtain a cellular suspension or monolayer.

2. A measurable substrate: Without being bound by a particular substrate formulation, a protein, peptide, cell-associated or synthetic organic compound based substrate of either broad metzincin specificity or more restricted specificity will be employed, which may be added in excess to the treated assay sample to initiate catalysis in some embodiments. In some embodiments, the measurable substrate may be a known target of a particular metzincin expressed on a cell and is therefore measured in the cell supernatant, e.g., a shed cell surface protein.

3. A substrate cleavage detection mechanism: Without being bound by any particular substrate cleavage detection mechanism, the assay will contain a mechanism to determine quantitatively the hydrolysis of the substrate by the targeted metzincin(s) present within the assay sample. The detection mechanism could employ fluorescence energy transfer quenching technology, colorimetric technology, luminescence technology, radio isotopic technology or chemiluminescence technology. The detection mechanism may require the application of separation techniques to demarcate for measurement purposes the cleaved substrate from the remaining reaction mixture containing the treated biological sample. For example, the determination of an amount of a shed protein substrate within a cell supernatant by the use of an ELISA assay specific for the said shed protein substrate or similar method 4. A catalytic cleft-directed antibody with neutralising specificity for individual members of ADAM, MMP and/or other metzincin protease families, for example, reprolysins, matrixins, or other subfamilies of metzincins: The term "antibody" as used herein refers to immunoglobulin molecules or other molecules which comprise at least one antigen binding domain. The term "antibody" as used herein is intended to include whole antibodies (IgG, IgE, IgA, IgM or IgD), polyclonal antibodies, monoclonal antibodies, humanised, chimeric antibodies, human antibodies, totally synthetic and recombinant antibodies, single chain antibodies, other forms of antibodies or specific epitope-binding agents, or any combination thereof.

In some embodiments, the assay may comprise the above key components in several reaction mixtures formulated to determine the degree of catalytic activity in the biological sample that is attributable to the target metzincin. In some aspects, the reaction mixture, may contain differing amounts of the treated biological sample. In certain embodiments, the amount of inhibitory catalytic cleft-directed antibody may be varied. In some embodiments, the reaction mixture will contain an excess of the exogenous substrate. In some embodiments, the catalytic cleft-directed antibody(s) developed to target and neutralise a specific metzincin activity is added to the treated sample prior to the initiation of the catalytic reaction via the addition of the exogenous substrate. The hydrolysis of the substrate may be followed to completion in the presence of the inhibitory antibody and the reaction profile may be compared to an identical reaction mixture in which the inhibitory catalytic cleft-directed antibody is replaced by a non-antigen binding control antibody. The reduction in the rate and extent of catalysis in antibody-inhibited sample compared to non-inhibited sample can be used to determine the catalytic activity attributable to the targeted metzincin. In some aspects of the assay design, precise quantification of the amount of target metzincin present in the biological sample can be obtained by determination of the change in rate constants for the enzymatic reaction in the presence and absence of inhibitory antibody. The use of a standardisation reaction scheme employing the cleavage of the substrate under zero order kinetics in the presence of a homogenous preparation of the target metzincin will allow the formation of a standard curve of reaction rate versus metzincin concentration thereby allowing the amount of target metzincin in the sample to be estimated.

It should be appreciated that any suitable assay format may be used, including, but not limited to, a solution-based assay, an immobilized substrate, a cell-based assay, an in-vitro assay, an ELISA, a multi-well format, a microfluidic format, any appropriate high throughput format, etc., or any combination thereof depending upon the class of metzincin to be measured. It also should be appreciated that any suitable detection technique may be used for substrate cleavage (e.g. fluorescent, bioluminescent, chemiluminescent, isotopic, etc., or any combination thereof). For example, the membrane associated MMPs (MT-MMPs) and ADAMs only demonstrate catalytic activity in a native membrane environment, thus necessitating the use of cell/tissue based assays. By way of example, non-fixed benign and tumour tissue samples can be collected and cells isolated using commercially available cell isolation kits. Briefly, tissue can be diced and deposited into appropriate cell media. Cells can be fragmented from tissue by enzymatic digestion with a combination of collagenase and DNAse for the required incubation period. The suspension can be filtered using 70-100 μm sterile mesh filter to remove larger undigested material. The filtered suspension can be centrifuged at 1200 rpm for 5 minutes to isolate cells or cell sorted by FACs or immunobead technology. The cells can be suspended in appropriate cell media at the required cell count or plated to form monolayers. Metzincin activity in these isolated cells can be measured in several ways: some potential assays are described below by way of example.

a) The cell sample can be assayed in a 96-well polystyrene plate containing a commercially available fluorogenic broad spectrum MMP substrate such as, OmniMMP™ fluorogenic substrate (Mca-Pro-Leu-Gly-Leu-Dpa-Ala-Arg-NH2.AcOH [Mca=(7-methoxycoumarin-4-yl)acetyl; Dpa=N-3-(2,4-dinitrophenyl)-L-a,β-diaminopropionyl]. The fluorescence can be followed at excitation 328 nm and emission 393 nm and relative fluorescence units compared between different experimental groups. To determine the specific metzincin activity, equivalent samples would be pre-treated with an isotype-specific metzincin-selective catalytic activity neutralizing antibody or control antibody and the difference in activity between the two treated samples would yield the specific activity of the metzincin subtype being investigated.

b) The cells isolated from a tissue sample can be used to determine metzincin shedding activity. For example, known endogenously released substrates can be measured in the supernatants derived from the isolated cells using an ELISA or similar quantitative detection system specific for the known substrate (e.g. HB-EGF for ADAM 12). Alternatively, a known substrate for the target metzincin can be developed as an enzyme-tagged construct (e.g. alkaline phosphatase-tag) which is transiently transfected into the isolated cells and the shedding determined as a measure of the tag enzyme activity in the supernatant (shedding assay, ref). To determine the specific metzincin activity, equivalent samples would be pre-treated with the isotype-specific metzincin-selective catalytic activity neutralizing antibody or control antibody and the difference in levels of the shed protein in the two samples would yield the specific activity of the metzincin metalloprotease being investigated.

A standard immunization protocol may be used to generate a catalytic-cleft directed antibody (e.g., as described in Rahman et al (33,34)). However, according to aspects of the invention, the defining feature of an immunization protocol is the use of unique immunogenic peptide antigens encompassing the metzincin catalytic cleft consensus sequence and flanking residues (e.g., amino acid $Ile^{346}$-$Asp^{359}$ of ADAM 15 SEQ ID NO: 7, Table 3), thereby eliciting antibodies directed towards the catalytic cleft of the target metalloendoproteinase. For ADAM 15, the specific, catalysis-neutralising antibodies obtained showed specificity for an epitope defined within an eight residue stretch incorporating the hallmark glycine ($His^{352}$-$Asp^{359}$). This region may, therefore, represent an important immunogenic area (consensus sequence HXBGBXHZ (SEQ ID NO: 5) or HXBGBXDZ (SEQ ID NO: 6), where X denotes any amino acid, B a variable bulky non-polar residue and Z is either a conserved aspartate, serine/threonine, glutamate, valine or proline depending on the subfamily identity) to which antibodies of exquisite specificity bind to the catalytic cleft of a target metzincin promoting the inhibition of catalytic activity. The specificity appears to be conferred by the combinations of the amino acids denoted by X, B and Z, where identity of the amino acids at positions X and B confer individual metzincin specificity and the amino acid at position Z may confer subfamily specificity or a combination of both aspects. Therefore, the assay described herein necessitates the development of neutralising antibodies directed to the catalytic cleft of the target metalloendoproteinase employing the use of peptide immunogens corresponding to the catalytic cleft immunogenic peptide encompassing the region described herein or peptides from the same vicinity that incorporate part of the region described herein. The development and application of such antibodies to the assay design represents the novel and inventive features of the present art. It is predicted, therefore by way of example that a peptide immunogen for human ADAM 12 corresponding to but not limited to the region $^{345}$LAHELGHNFGMNHD$^{358}$ (SEQ ID NO: 10) would generate a selective antibody that would likely recognise an epitope within but not restricted to the sequence 351HNFGMNHD358 (SEQ ID NO: 43). Likewise, a peptide immunogen for human ADAM 17 encompassing the region $^{403}$TTHELGHNFGAEHD$^{416}$ (SEQ ID NO: 11) would generate a selective antibody that would likely recognises an epitope within but not restricted to the region $^{499}$HNFGAEHD$^{416}$ (SEQ ID NO: 44) and so on.

The patents and publications referred to herein are incorporated by reference in their entirety. In the event of conflict, the teachings of the present description shall control in the absence of clear error.

REFERENCES

1. WALTER STOCKER,' FRANK GRAMS, ULRICH BAUMANN, PETER REINEMER,'FRANZ-XAVER GOMIS-RUTH, DAVID B. McKAY,' AND WOLFRAM BODEMIKALA (1995). The metzincins-Topological and sequential relations between the astacins, adamalysins, serralysins, and matrixins (collagenases) define a superfamily of zinc-peptidases. Protein Science, 4:823-840.
2. F. XAVIER GOMIS-RUTH (2009) Catalytic Domain Architecture of Metzincin Metalloendoproteinases. J. Biol. Chem. 284, 15353-15358.

3. MIKALA EGEBLAD AND ZENA WERB (2002). New functions for the matrix metalloproteinases in cancer progression Nature Reviews Cancer 2. 161-174
4. MURPHY G. (2008). The ADAMs: Signalling scissors in the tumour microenvironment. Nature Reviews Cancer. 8, 929-941.
5. ADAM R. JOHNSON, ALEXANDER G. PAVLOVSKY, DANIEL F. ORTWINE, et al (2007). Discovery and Characterization of a Novel Inhibitor of Matrix Metalloprotease-13 That Reduces Cartilage Damage in Vivo without Joint Fibroplasia Side Effects 2007, J. Biol. Chem. 282, pp. 27781-27791.
6. SANTIAGO RIVERA, MICHEL KHRESTCHATISKY, LESZEK KACZMAREK, GARY A. ROSENBERG, AND DIANE M. JAWORSKI (2010). Metzincin Proteases and their Inhibitors, Foes or Friends in Nervous System Physiology? J. Neurosci. 17; 30(46): 15337-15357.
7. MCGOWAN P M, RYAN B M, HILL A D K, ET AL. ADAM-17 expression correlates with parameters of tumor progression. Clin Cancer Res 2007; 13:2335-43.
8. CHRISTOPHER M. OVERALL AND ODED KLEIFELD (2006). Validating matrix metalloproteinases as drug targets and anti-targets for cancer therapy Nature Reviews Cancer 6, 227-239.
9. FRIDMAN J S, CAULDER E, HANSBURY M, ET AL. Selective inhibition of ADAM metalloproteases as a novel approach for modulating ErbB pathways in cancer. Clin Cancer Res 2007; 13:1892-902.
10. ZHOU B-B S, PETYON M, HE B, ET AL. Targeting ADAM-mediated ligand cleavage to inhibit HER2 and EGFR pathways in non-small cell lung cancer. Cancer Cell 2006; 10:39-50.
11. ROY R, WEWER U M, ZURAKOWSKI D, PORIES S E, MOSES M A. ADAM 12 cleaves extracellular matrix proteins and correlates with cancer status andstage. Biol Chem 2004; 279: 51 323-30.
12. KODAMA T, IKEDA E, OKADA A ET AL. ADAM 12 is selectively overexpressed in human glioblastomas and is associated with glioblastoma cell proliferation and shedding of heparin-binding epidermal growth factor. Am J Pathol 2004; 165: 1743-53.
13. YANG, W. et al. (2001). Human macrophage metalloelastase gene expression in colorectal carcinoma and its clinicopathologic significance. Cancer 91, 1277-1283.
14. BLOBEL C P. (2005). ADAMs: Key players in EGF signalling, development and disease. Nature Revs Mol. Cell. Biol. 6, 32-45.
15. LUCAS, N & DAY, M L (2009). The role of the disintegrin metalloendoproteinase ADAM 15 in prostate cancer progression. J. Cell. Biochem. 106, 967-974.
16. ZHONG, J L, POGHOSYAN, Z., PENNINGTON, C J et al. (2008). Distinct functions of natural ADAM-15 cytoplasmic domain variants in human mammary carcinoma. Mol. Cancer. Res. 6, 383-394.
17. MARETZKY, T., LE GALL., SM., et al. (2009). Src stimulates fibroblast growth factor receptor-2 shedding by an ADAM 15 splice variant linked to breast cancer. Cancer Res. 69, 4573-4576.
18. HUXLEY-JONES ET AL. (2007). BMC Evolutionary Biology 7:63 doi:10.1186/1471-2148-7-63
19. LEVY G G, MOTTO D G, GINSBURG D (2005). "ADAMTS13 turns 3.". Blood 106 (1): 11-7
20. GAVIN C JONES AND GRAHAM P RILEY (2005). ADAMTS proteinases: a multi-domain, multi-functional family with roles in extracellular matrix turnover and arthritis. Arthritis research & Therapy 7, 160-170.
21. REILLY M P, LI M, HE J, FERGUSON J F, STYLIANOU I M, MEHTA N N, BURNETT M S, et al (2011). Identification of ADAMTS7 as a novel locus for coronary atherosclerosis and association of ABO with myocardial infarction in the presence of coronary atherosclerosis: two genome-wide association studies. Myocardial Infarction Genetics Consortium; Wellcome Trust Case Control Consortium, Martinelli N, Girelli D, Quyyumi A A, Anderson J L, Erdmann J, Hall A S, Schunkert H, Quertermous T, Blankenberg S, Hazen S L, Roberts R, Kathiresan S, Samani N J, Epstein S E, Rader D J. Lancet. 29; 377(9763):383-92.
22. RENEE E. YURA, I S. GAYLEN BRADLEY, I GANESAN RAMESH, 2 W. BRIAN REEVES, 2 AND JUDITH S. BOND (2009). Meprin A metalloproteases enhance renal damage and bladder inflammation after LPS challenge Am J Physiol Renal Physiol 296: F135-F144.
23. BOND J S, MATTERS G L, BANERJEE S, DUSHECK R E. (2005). Meprin metalloprotease expression and regulation in kidney, intestine, urinary tract infections and cancer. FEBS Lett 579: 3317-3322, 2005.
24. GE G, GREENSPAN DS (2006). Developmental roles of the BMP1/TLD metalloproteinases. Birth Defects Res C Embryo Today 78:47-68
25. WINN V D, GORMLEY M, PAQUET A C, KJAERSORENSEN K, KRAMER A, RUMER K K, HAIMOV-KOCHMAN R, YEH R F, OVERGAARD M T, VARKI A, OXVIG C, FISHER S J. (2009). Severe preeclampsia-related changes in gene expression at the maternal-fetal interface include sialic acid-binding immunoglobulin-like lectin-6 and pappalysin-2 Endocrinology. 2009 January; 150(1):452-62.
26. DEVEL L, CZARNY B, BEAU F, GEORGIADIS D, STURA E, DIVE V. (2010). Third generation of matrix metalloendoproteinase inhibitors: Gain in selectivity by targeting the depth of the S(1)' cavity. Biochimie. 2010 Aug. 7. [Epub ahead of print]
27. CARINE LOMBARD, JOELLE SAULNIER, JEAN WALLACH (2005). Assays of matrix metalloproteinases (MMPs) activities: a review. Biochimie 87, 265-272.
28. Jan H. VERHEIJEN*, Nancy M. E. NIEUWENBROEK*, Bob BEEKMAN*, Roeland HANEMAAIJER*, Hein W. VERSPAGET<, H. Karel RONDAY*E and Arjen H. F. BAKKER (1997) Modified proenzymes as artificial substrates for proteolytic enzymes: colorimetric assay of bacterial collagenase and matrix metalloproteinase activity using modified pro-urokinase. Biochem. J. 323, 603-609
29. ROELAND HANEMAAIJER, HETTY VISSER, YR30 T. KONTTINEN*, PIETER KOOLWIJK and JAN H. VERHEIJEN A Novel and Simple Immunocapture Assay for Determination of Getatinase-B (MMP-9) Activities in Biological Ftuids: Saliva from Patients with SjiSgren's Syndrome Contain Increased Latent and Active Gelatinase-B Levels
30. MARCIA L. MOSS, AND FRED H. RASMUSSEN (2007). Fluorescent substrates for the proteinases ADAM 17, ADAM 10, ADAM8, and ADAM 12 useful for high-throughput inhibitor screening Analytical Biochemistry 366, pp 144-148.
31. G. JIN, X. HUANG, R. BLACK, M. WOLFSON, C. RAUCH, H. MCGREGOR, G. ELLESTAD AND R. COWLING, A continuous fluorimetric assay for tumor necrosis factor-alpha converting enzyme, Anal. Biochem. 302 (2002), pp. 269-275
32. ANNE M. FOURIE‡, FAWN COLES, VERONICA MORENO, AND LARS KARLSSON (2003). Catalytic Activity of ADAMS, ADAM15, and MDC-L (ADAM28) on Synthetic Peptide Substrates and in Ectodomain Cleavage of CD23 J. OF BIOL. CHEM. 278, pp. 30469-30477.
33. RAHMAN, S., PATEL, Y., GERHARDT, H & LUNDKVIST, A (2008). Antibodies. U.S. provional patent application US 61/038,837
34. RAHMAN, S., PATEL, Y., GERHARDT, H & LUNDKVIST, A (2009). ADAM 15 antibodies and immunogenic peptides. PCT application PCT/IB2009/00561
35. MARETZKY, T., YANG, G., OUERFELLI, O. et al. (2009) Characterisation of the catalytic activity of the membrane anchored metalloproteinase ADAM 15 in cell-based assays. Biochem. J. 420, 105-113.
36. GALVEZ, B. G., MATIAS-ROMAN, S., ALBAR, J. P., SANCHEZ-MADRID, F. & ARROYO, A. G. (2001) Membrane type 1-matrix metalloproteinase is activated during migration of human endothelial cells and modulates endothelial motility and matrix remodeling. J. Biol. Chem. 276, 37491-37500

What is claimed herein is:

1. An isolated antibody or antigen-binding fragment thereof that
selectively binds to a protease-specific epitope encompassed within a peptide sequence selected from SEQ ID NOs: 9, 10, 11, 12, 14, 17, 20, 21, 24 and 33 of the metzincin protease catalytic cleft region.

2. The isolated antibody or antigen-binding fragment thereof according to claim 1, wherein the protease-specific epitope comprises a peptide sequence selected from SEQ ID NOs: 9, 10, 11, 12, 14, 17, 20, 21, 24 and 33.

3. The isolated antibody or antigen binding fragment thereof according to claim 1, wherein the isolated antibody or antigen-binding fragment thereof is a mouse, mammalian, monoclonal, polyclonal, humanized, human, chimeric, synthetic, recombinant, and/or a single chain antibody.

4. The isolated antibody or antigen-binding fragment thereof according to claim 1, wherein the isolated antibody is raised by immunizing a host animal with a peptide comprising the protease-specific epitope.

5. The isolated antibody or antigen-binding fragment thereof according to claim 1, wherein the isolated antibody is raised in vitro.

6. A method of treating cancer comprising administering to a subject the isolated antibody or antigen-binding fragment thereof of claim 1.

7. The method of claim 6, wherein the isolated antibody or antigen binding fragment thereof is administered in combination with an anti-neoplastic agent and/or an anti-angiogenic agent.

8. The isolated antibody or antigen binding fragment thereof according to claim 1, wherein the isolated antibody is raised against an epitope encompassed within a peptide consisting of an amino acid sequence selected from 9, 10, 11, 12, 14, 17, 20, 21, 24 and 33.

9. The isolated antibody or antigen-binding fragment thereof according to claim 4, wherein the isolated antibody is raised in vitro.

10. The isolated antibody or antigen-binding fragment thereof according to claim 8, wherein the isolated antibody is raised in vitro.

11. The isolated antibody or antigen-binding fragment thereof according to claim 1, wherein the protease-specific epitope consists of a peptide sequence selected from SEQ ID NOs: 9, 10, 11, 12, 14, 17, 20, 21, 24 and 33.

\* \* \* \* \*